US012702428B2

(12) United States Patent
Vaughan et al.

(10) Patent No.: US 12,702,428 B2
(45) Date of Patent: Aug. 11, 2026

(54) ROTARY SURGICAL CUTTING TOOL AND RELATED ACCESSORIES

(71) Applicant: Stryker European Operations Limited, Carrigtwohill (IE)

(72) Inventors: Aidan Vaughan, Cork City (IE); Eoin Connolly, Dublin (IE); David Eustace, Carrigrohane (IE); Conor O'Shea, Innishannon (IE)

(73) Assignee: Stryker European Operations Limited, Carrigtwohill (IE)

( * ) Notice: Subject to any disclaimer, the term of this patent is extended or adjusted under 35 U.S.C. 154(b) by 527 days.

(21) Appl. No.: 17/616,738

(22) PCT Filed: Jun. 5, 2020

(86) PCT No.: PCT/IB2020/055338

§ 371 (c)(1),
(2) Date: Dec. 6, 2021

(87) PCT Pub. No.: WO2020/245802

PCT Pub. Date: Dec. 10, 2020

(65) Prior Publication Data

US 2022/0296254 A1 Sep. 22, 2022

Related U.S. Application Data

(60) Provisional application No. 62/972,354, filed on Feb. 10, 2020, provisional application No. 62/857,959, filed on Jun. 6, 2019.

(51) Int. Cl.
*A61B 17/16* (2006.01)

(52) U.S. Cl.
CPC ...... *A61B 17/1622* (2013.01); *A61B 17/1615* (2013.01); *A61B 17/162* (2013.01); *A61B 17/1633* (2013.01); *A61B 17/1659* (2013.01)

(58) Field of Classification Search
CPC .. A61C 3/02–03; A61B 17/1613–1624; A61B 17/1631–1633; A61B 17/1659;
(Continued)

(56) References Cited

U.S. PATENT DOCUMENTS 921,547 A 5/1909 Kruger
1,766,136 A 6/1930 Markstrum
(Continued)

FOREIGN PATENT DOCUMENTS

CN 102333490 A 1/2012
CN 106714707 A 5/2017
(Continued)

OTHER PUBLICATIONS

English language abstract for CN 102333490 A extracted from espacenet.com database on Dec. 5, 2023, 2 pages.
(Continued)

*Primary Examiner* — Elizabeth Houston
*Assistant Examiner* — Jonathan A Hollm
(74) *Attorney, Agent, or Firm* — Howard & Howard Attorneys PLLC

(57) ABSTRACT

A surgical handpiece system (10) includes a high-speed surgical bur assembly (102) and a surgical handpiece assembly (104). The high-speed surgical bur assembly has a nose tube (17, 106) and a driveshaft (24, 110) at least partially disposed within the nose tube. A cutting tool (18, 114) is coupled to a distal region of the driveshaft. The cutting tool and the driveshaft are configured to rotate relative to the nose tube. The surgical handpiece system comprises a hub (14, 146) and a rotatable drive chuck (30, 34, 172) for alignment and coupling to the nose tube and the driveshaft. A motor (12) is configured to rotate the rotatable drive chuck, the driveshaft, and the cutting tool when the driveshaft is coupled to the rotatable drive chuck.

14 Claims, 18 Drawing Sheets

(58) Field of Classification Search
CPC ........ A61B 17/1695; A61B 17/320758; A61B 17/32002; A61B 17/32; A61B 2017/320766–320775; A61B 2017/320024–320032; A61B 2017/320004–320012
See application file for complete search history.

(56) References Cited

U.S. PATENT DOCUMENTS 2,219,907 A 10/1940 Ross
2,419,045 A 4/1947 Whittaker
2,936,034 A 5/1960 Van Der Lely et al.
3,093,982 A 6/1963 Staeger
3,498,351 A 3/1970 Edwards et al.
3,604,487 A 9/1971 Gilbert
4,578,608 A 3/1986 Mech et al.
4,581,963 A 4/1986 Kim
4,587,909 A 5/1986 Bailey
4,704,929 A 11/1987 Osada
4,763,548 A 8/1988 Leibinger et al.
4,811,736 A 3/1989 Griggs et al.
4,844,609 A 7/1989 Floyd et al.
4,963,144 A 10/1990 Huene
5,052,253 A 10/1991 Lin
5,139,499 A 8/1992 Small et al.
5,222,956 A 6/1993 Waldron
5,405,348 A 4/1995 Anspach et al.
5,431,660 A 7/1995 Burke
5,484,440 A 1/1996 Allard
5,520,696 A 5/1996 Wenstrom, Jr.
5,649,931 A 7/1997 Bryant et al.
5,667,513 A 9/1997 Torrie
5,762,344 A 6/1998 Einvall
5,833,704 A 11/1998 McCombs et al.
5,976,165 A 11/1999 Ball et al.
6,033,408 A 3/2000 Gage et al.
6,053,508 A 4/2000 Kuhl
6,068,642 A 5/2000 Johnson et al.
6,132,435 A 10/2000 Young
6,173,146 B1 1/2001 Wang et al.
6,189,422 B1 2/2001 Stihl
6,203,238 B1 3/2001 Otto
6,250,858 B1 6/2001 Salyer
6,276,879 B1 8/2001 Hecht
6,287,313 B1 9/2001 Sasso
6,305,867 B1 10/2001 Schweigert et al.
6,339,868 B1 1/2002 Nagaya et al.
6,402,759 B1 6/2002 Strong et al.
6,415,693 B1 7/2002 Simon et al.
6,598,498 B1 7/2003 Pigford et al.
6,854,742 B2 2/2005 Salyer et al.
6,857,343 B1 2/2005 Easterbrooks et al.
6,877,402 B1 4/2005 Pigford et al.
6,949,101 B2 9/2005 McCleary et al.
7,001,391 B2 2/2006 Estes et al.
7,011,661 B2 3/2006 Riedel et al.
7,060,071 B2 6/2006 Steiger
7,066,940 B2 6/2006 Riedel
7,243,580 B2 7/2007 Frazee
7,326,214 B2 2/2008 Michelson
7,326,215 B2 2/2008 Myers et al.
7,341,587 B2 3/2008 Molz, IV et al.
7,399,303 B2 7/2008 Michelson
7,488,322 B2 2/2009 Brunnett et al.
7,559,927 B2* 7/2009 Shores ................ A61B 17/162 606/79
7,658,740 B2 2/2010 Shores et al.
7,766,585 B2 8/2010 Vasudeva et al.
7,879,037 B2 2/2011 Brunnett et al.
7,892,235 B2 2/2011 Ellis
7,992,878 B2 8/2011 Dace
8,016,523 B2 9/2011 Vasudeva et al.
8,357,163 B2 1/2013 Sidebotham et al.
8,371,744 B2 2/2013 Walter et al.
8,403,931 B2 3/2013 Sidebotham et al.
8,449,545 B2 5/2013 Sidebotham et al.
8,460,297 B2 6/2013 Watlington et al.
8,518,043 B2 8/2013 Sidebotham et al.
8,518,044 B2 8/2013 Sidebotham et al.
8,523,866 B2 9/2013 Sidebotham et al.
8,535,316 B2 9/2013 Lewis et al.
8,540,716 B2 9/2013 Sidebotham et al.
8,556,897 B2 10/2013 Sidebotham et al.
8,568,415 B2 10/2013 Brunnett et al.
8,690,876 B2 4/2014 Del Rio et al.
8,801,713 B2 8/2014 Del Rio et al.
8,870,873 B2 10/2014 Del Rio et al.
8,939,979 B2 1/2015 Del Rio et al.
9,113,917 B2 8/2015 Del Rio et al.
9,181,984 B2 11/2015 Beard et al.
9,186,157 B2 11/2015 Brunnett et al.
9,381,023 B2 7/2016 Del Rio et al.
9,402,638 B2 8/2016 Del Rio et al.
9,427,279 B2 8/2016 Muniz-Medina et al.
9,451,954 B2 9/2016 Moore et al.
9,463,028 B2 10/2016 Sidebotham et al.
D782,042 S 3/2017 Dexter et al.
D790,699 S 6/2017 Dexter et al.
9,681,879 B2 6/2017 Del Rio et al.
9,687,257 B2 6/2017 Straslicka et al.
9,750,526 B2 9/2017 Higgins et al.
9,764,389 B2 9/2017 Kobayashi
D800,903 S 10/2017 Heiliger
D800,906 S 10/2017 Cihak
D800,907 S 10/2017 Cihak
9,820,756 B2 11/2017 Del Rio et al.
9,877,763 B2 1/2018 Barth et al.
9,907,559 B2 3/2018 Del Rio et al.
10,080,579 B2 9/2018 Cihak et al.
10,092,300 B2 10/2018 Del Rio et al.
10,111,692 B2 10/2018 Baker et al.
10,111,698 B2 10/2018 Scheib et al.
10,470,786 B2 11/2019 Deeny et al.
10,940,013 B2 3/2021 Puno
10,966,743 B2 4/2021 Cushen et al.
11,819,221 B2 11/2023 Burke
11,896,314 B2 2/2024 Bozung
2002/0058958 A1 5/2002 Walen
2003/0060829 A1 3/2003 Del Rio et al.
2003/0063823 A1 4/2003 Del Rio et al.
2003/0125750 A1 7/2003 Zwirnmann et al.
2003/0130663 A1 7/2003 Walen
2003/0163134 A1 8/2003 Riedel et al.
2004/0221688 A1 11/2004 Liao
2004/0248746 A1 12/2004 Matsui
2005/0177168 A1 8/2005 Brunnett et al.
2006/0241630 A1* 10/2006 Brunnett ............ A61B 17/1624 606/80
2007/0005077 A1 1/2007 Null et al.
2007/0276403 A1 11/2007 Franks et al.
2008/0243133 A1 10/2008 Heinz
2011/0031505 A1 2/2011 Harada et al.
2012/0221035 A1 8/2012 Harvey
2015/0238241 A1 8/2015 Barth et al.
2016/0278788 A1 9/2016 Dexter et al.
2016/0278802 A1 9/2016 Cihak et al.
2017/0035444 A1 2/2017 Carrison et al.
2017/0159717 A1 6/2017 Marchand et al.
2017/0281196 A1 10/2017 Del Rio et al.
2017/0354431 A1 12/2017 Rubin et al.
2018/0036026 A1 2/2018 Namdar
2018/0110572 A1* 4/2018 Flatt ...................... A61B 34/30
2018/0132865 A1 5/2018 Del Rio et al.
2018/0242962 A1 8/2018 Walen et al.
2018/0256174 A1 9/2018 Deeny et al.
2018/0325529 A1 11/2018 del Rio et al.
2018/0353201 A1 12/2018 Cihak et al.
2018/0353232 A1 12/2018 Barth et al.

(56) References Cited

U.S. PATENT DOCUMENTS

| | | | |
|---|---|---|---|
| 2019/0388115 | A1 | 12/2019 | Nguyen |
| 2022/0296254 | A1 | 9/2022 | Vaughan et al. |

FOREIGN PATENT DOCUMENTS

| | | | |
|---|---|---|---|
| EP | 0634146 | A2 | 1/1995 |
| EP | 1155776 | A2 | 11/2001 |
| FR | 1166884 | A | 11/1958 |
| FR | 2558224 | A1 | 7/1985 |
| JP | H01240615 | A | 9/1989 |
| JP | 2003021213 | A | 1/2003 |
| JP | 2010534528 | A | 11/2010 |
| JP | 2018108439 | A | 7/2018 |
| JP | 7645200 | B2 | 3/2025 |
| RU | 2191898 | C2 | 10/2002 |
| WO | WO0160261 | A2 | 8/2001 |
| WO | 03025102 | A1 | 3/2003 |
| WO | 03035168 | A1 | 5/2003 |
| WO | 2004043271 | A1 | 5/2004 |
| WO | 2012138337 | A1 | 10/2012 |
| WO | 2015123548 | A1 | 8/2015 |
| WO | 2018026369 | A1 | 2/2018 |
| WO | 2018122687 | A1 | 7/2018 |

OTHER PUBLICATIONS

English language abstract for CN 106714707 A extracted from espacenet.com database on Dec. 5, 2023, 2 pages.

English language abstract for JP 2010-534528 A extracted from espacenet.com database on Feb. 22, 2024 2 pages.

English language abstract for JP 2018-108439 A extracted from espacenet.com database on Feb. 22, 2024 2 pages.

Partial International Search Report for Application No. PCT/IB2020/055338 dated Nov. 25, 2020, 2 pages.

International Search Report for Application No. PCT/IB2020/055338 dated Apr. 19, 2021, 3 pages.

English language abstract and machine-assisted English translation for EP 0 634 146 A2 extracted from espacenet.com database on Feb. 16, 2022, 8 pages.

English language abstract and machine-assisted English translation for EP 1 155 776 A2 extracted from espacenet.com database on Feb. 16, 2022, 17 pages.

Machine-assisted English translation for FR 1 166 884 A extracted from espacenet.com database on Feb. 16, 2022, 4 pages.

English language abstract and machine-assisted English translation fo FR 2 558 224 A1 extracted from espacenet.com database on Feb. 16, 2022, 7 pages.

English language abstract and machine-assisted English translation for JPH 01-240615 A extracted from espacenet.com database on Feb. 16, 2022, 6 pages.

English language abstract and machine-assisted English translation for JP 2003-021213 A extracted from espacenet.com database on Feb. 16, 2022, 10 pages.

English language abstract and machine-assisted English translation for RU 2 191 898 C2 extracted from espacenet.com database on Feb. 16, 2022, 7 pages.

English language abstract for WO 03/025102 A1 extracted from espacenet.com database on Feb. 16, 2022, 2 pages.

English language abstract for JP 7645200 B2 extracted from espacenet.com database on Jan. 6, 2026, 1 page.

* cited by examiner 12
10
2,3
14
20
22
3
17
16
21
18
2

42
40
34
20
44
62
46
24
50
48
75
72
66
52
74
14
60
54
58
54
56
16

16
17
18
20
24
34
42
48
50
52
56
66
72
74

100
146
104

106
102
118
114

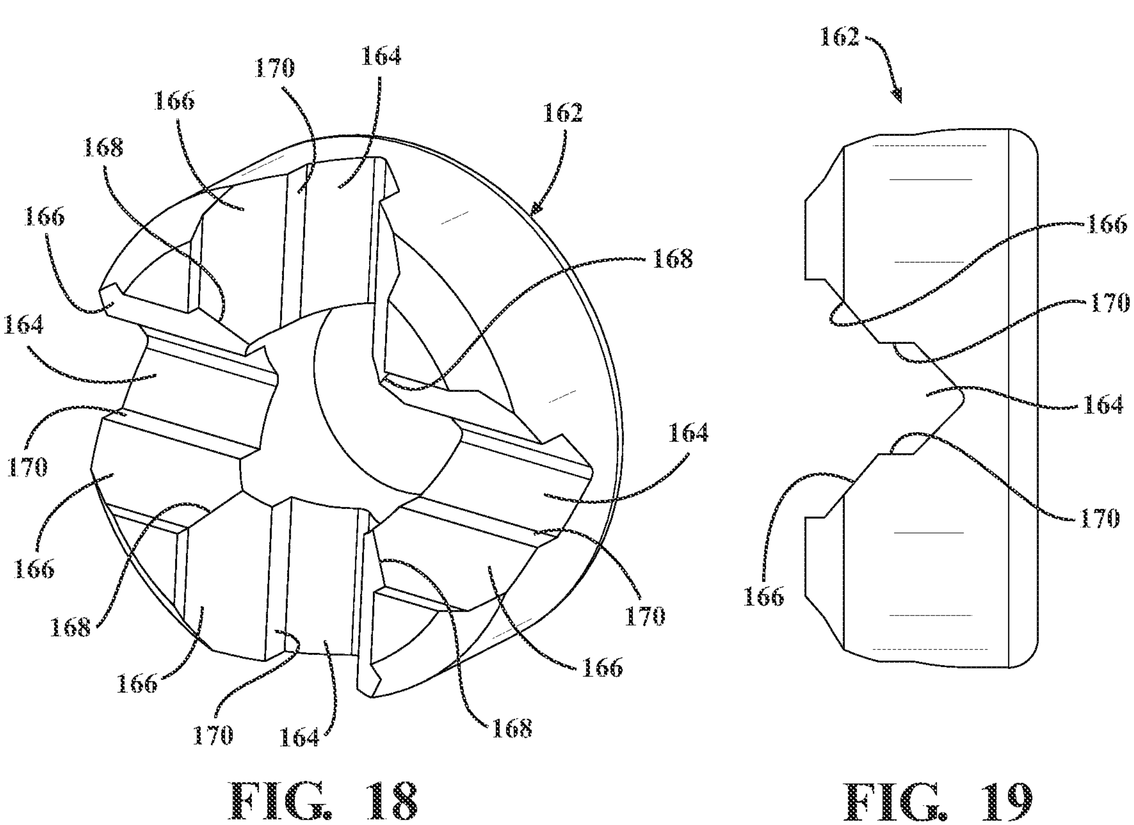
FIG. 18
FIG. 19
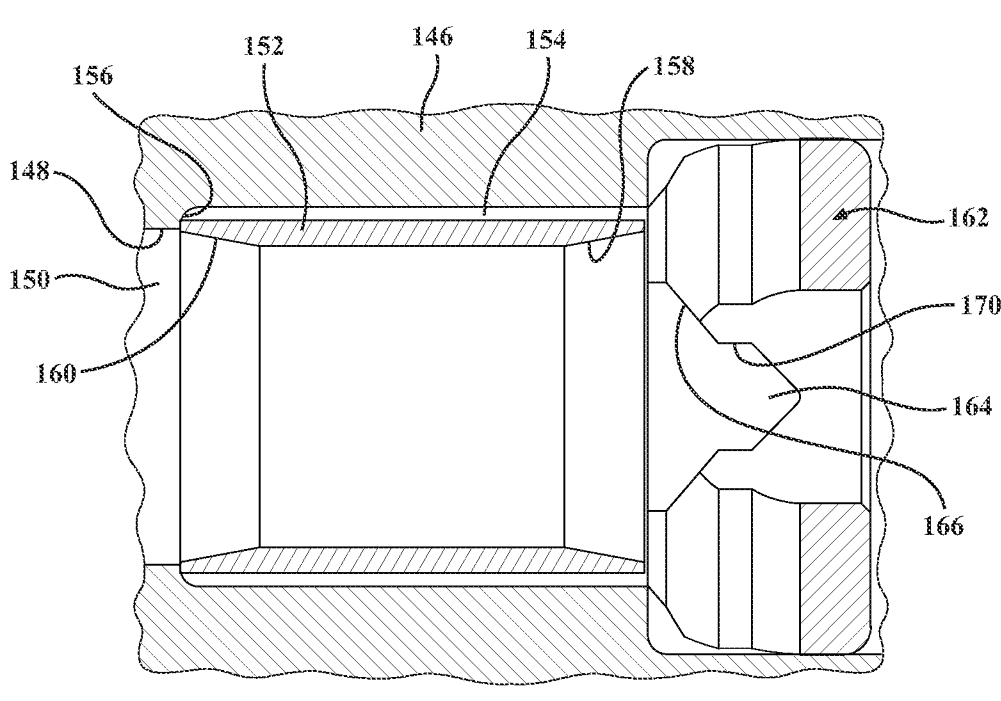
FIG. 20

ROTARY SURGICAL CUTTING TOOL AND RELATED ACCESSORIES

RELATED APPLICATIONS

The subject patent application is the National Stage entry of International Patent Application No. PCT/IB2020/055338, filed Jun. 5, 2020, which claims priority to and all the benefits of U.S. Provisional Patent Application No. 62/972,354, filed on Feb. 10, 2020, and U.S. Provisional Patent Application No. 62/857,959, filed on Jun. 6, 2019, the entire contents of which are hereby incorporated by reference.

BACKGROUND

High-speed burs often include motors and separate disposable components. The disposable component must be coupled to the motor in such a way that torque can be transferred from the motor, through a driveshaft to rotate a cutting bur at a high rate of speed to erode and/or abrade a surface. It is an object of this disclosure to improve this coupling.

SUMMARY

The present disclosure relates generally to a surgical handpiece system. An exemplary configuration provides a surgical handpiece system having a high-speed surgical bur assembly. The high-speed surgical bur assembly includes a nose tube defining a lumen extending between proximal and distal ends of the nose tube. The nose tube has a proximal portion extending along an axis. The proximal portion of the nose tube has an outer surface defining a nose tube recess. The nose tube also includes a projection disposed proximal to the nose tube recess. The high-speed surgical bur assembly also includes a driveshaft at least partially disposed within the lumen of the nose tube and configured to rotate relative to the nose tube. The high-speed surgical bur assembly also includes a cutting tool coupled to a distal region of the driveshaft. The cutting tool is configured to rotate with the driveshaft relative to the nose tube. The system also includes a surgical handpiece assembly including a hub having a bore defining a cavity for receiving the proximal portion of the nose tube of the high-speed surgical bur assembly. The surgical handpiece assembly also includes a biasing member disposed within the cavity of the hub. The biasing member is configured to be received by the nose tube recess of the nose tube to constrain a depth of the nose tube of the high-speed surgical bur assembly within the cavity of the hub relative to the hub. The surgical handpiece assembly also includes a radial alignment member disposed within the cavity of the hub proximal to the biasing member. The radial alignment member defines a notch for receiving the projection to constrain a radial orientation of the nose tube relative to the hub.

Another exemplary configuration provides a surgical handpiece system including a high-speed surgical bur assembly. The high-speed surgical bur assembly includes a nose tube defining a lumen extending between proximal and distal ends of the nose tube. The high-speed surgical bur assembly also includes a driveshaft at least partially disposed within the lumen of the nose tube and configured to rotate relative to the nose tube. The driveshaft has a proximal region extending along a driveshaft axis. The high-speed surgical bur assembly also includes a cutting tool coupled to a distal region of the driveshaft. The cutting tool is configured to rotate with the driveshaft relative to the nose tube. The system also includes a surgical handpiece assembly including a hub having a bore defining a cavity for receiving the proximal end of the nose tube of the high-speed surgical bur assembly and a proximal region of the driveshaft. The surgical handpiece assembly also includes a rotatable drive chuck configured to be rotated by a motor about a hub axis. The rotatable drive chuck is disposed within the cavity of the hub and configured to rotate relative to the hub. The rotatable drive chuck defines an opening for receiving the proximal region of the driveshaft. The rotatable drive chuck includes a driving portion disposed proximal the opening. The driving portion has at least two driving surfaces configured to engage the driveshaft in a driving orientation to rotate the driveshaft. The rotatable drive chuck also includes an aligning portion disposed between the driving portion and the opening of the rotatable drive chuck. The aligning portion has an alignment edge extending distally from the driving portion of the rotatable drive chuck toward the opening of the rotatable drive chuck. The alignment edge tapers away from the hub axis as the alignment edge extends distally from the driving portion of the rotatable drive chuck. The driveshaft is configured to engage the alignment edge of the aligning portion of the rotatable drive chuck to orient the driveshaft to the driving orientation for the driveshaft to engage the at least two driving surfaces of the driving portion of the rotatable drive chuck.

Yet another exemplary configuration provides a high-speed surgical bur assembly configured to cut tissue and to be coupled to a surgical handpiece assembly. The high-speed surgical bur assembly includes a nose tube defining a lumen extending between proximal and distal ends of the nose tube. The nose tube has a proximal portion extending along an axis. The proximal portion of the nose tube has an outer surface defining a recess for receiving a biasing member of the surgical handpiece assembly to constrain a depth of the nose tube relative to the surgical handpiece assembly. The nose tube includes a projection disposed proximal to the recess. The projection is configured to constrain a radial orientation of the nose tube relative to the surgical handpiece assembly. The high-speed surgical bur assembly also includes a driveshaft at least partially disposed within the lumen of the nose tube and configured to rotate relative to the nose tube. The driveshaft has a drive portion at a proximal region of the driveshaft for engaging a rotatable drive chuck of the surgical handpiece assembly. The high-speed surgical bur assembly also includes a cutting tool coupled to a distal region of the driveshaft opposite the drive portion. The cutting tool is configured to rotate with the driveshaft relative to the nose tube in response to rotation of the rotatable drive chuck of the surgical handpiece assembly.

Another exemplary configuration provides a high-speed surgical bur assembly configured to cut tissue and to be coupled to a surgical handpiece assembly. The high-speed surgical bur assembly includes a nose tube defining a lumen extending between proximal and distal ends of the nose tube. The nose tube has a proximal portion configured to be coupled to the surgical handpiece assembly. The proximal portion of the nose tube includes a projection configured to constrain a radial orientation of the nose tube relative to the surgical handpiece assembly. The high-speed surgical bur assembly also includes a driveshaft at least partially disposed within the lumen of the nose tube and configured to rotate relative to the nose tube. The driveshaft has a proximal region extending along an axis. The proximal region of the driveshaft includes a drive portion for engaging a rotatable drive chuck of the surgical handpiece assembly in a driving orientation. The driveshaft also includes an alignment portion proximal the drive portion of the driveshaft. The alignment portion has an outer surface tapering toward the axis as the alignment portion extends from the drive portion to a proximal end of the driveshaft. The alignment portion is configured to engage the rotatable drive chuck to align the drive portion to the driving orientation for the drive portion of the driveshaft to engage the rotatable drive chuck. The alignment portion defines a notch extending distally from the proximal end of the driveshaft for mitigating contact between the alignment portion of the driveshaft and the rotatable drive chuck during engagement of the alignment portion with the rotatable drive chuck. The high-speed surgical bur assembly also includes a cutting tool coupled to a distal region of the driveshaft opposite the proximal region of the driveshaft. The cutting tool is configured to rotate with the driveshaft relative to the nose tube in response to rotation of the rotatable drive chuck of the surgical handpiece assembly.

Yet another exemplary configuration provides a high-speed surgical bur assembly for connection to a surgical handpiece assembly. The high-speed surgical bur assembly includes a driveshaft having proximal and distal ends. The high-speed surgical bur assembly also includes a nose tube having a first region defining a lumen to at least partially receive the driveshaft between the proximal and distal ends. The high-speed surgical bur assembly also includes a second region extending monolithically from the first region to couple the driveshaft to the surgical handpiece assembly at the proximal end. The second region includes an alignment feature configured to radially align the nose tube to the surgical handpiece assembly. The second region also includes a retention feature configured to axially retain the nose tube to the surgical handpiece assembly. The high-speed surgical bur assembly also includes a cutting tool coupled to the driveshaft at the distal end of the driveshaft.

Another exemplary configuration provides a surgical handpiece assembly configured to be coupled to a high-speed surgical bur assembly having a nose tube and a driveshaft rotatably coupled to the nose tube. The surgical handpiece assembly includes a hub having a bore defining a cavity for receiving a proximal portion of the nose tube. The surgical handpiece assembly also includes a biasing member disposed within the cavity of the hub. The biasing member is configured to engage the nose tube to constrain a depth of the nose tube within the cavity of the hub relative to the hub. The surgical handpiece assembly also includes a radial alignment member disposed within the cavity of the hub proximal to the biasing member. The radial alignment member defines a notch for receiving a projection of the nose tube to constrain a radial orientation of the nose tube relative to the hub. The radial alignment member has an alignment wall extending distally from the notch for engaging the projection of the nose tube and radially positioning the nose tube to permit the notch to receive the projection of the nose tube.

BRIEF DESCRIPTION OF THE DRAWINGS

Advantages of the present disclosure will be readily appreciated as the same becomes better understood by reference to the following detailed description when considered in connection with the accompanying drawings.

FIG. 18 is a perspective view of a radial alignment member of the surgical handpiece assembly of FIG. 14.

FIG. 19 is a plan view of the radial alignment member of the surgical handpiece assembly of FIG. 14.

FIG. 20 is a detailed sectional view of the surgical handpiece assembly of FIG. 14 before the high-speed surgical bur assembly is inserted in a cavity of a hub of the surgical handpiece assembly.

DETAILED DESCRIPTION

Figure 1:
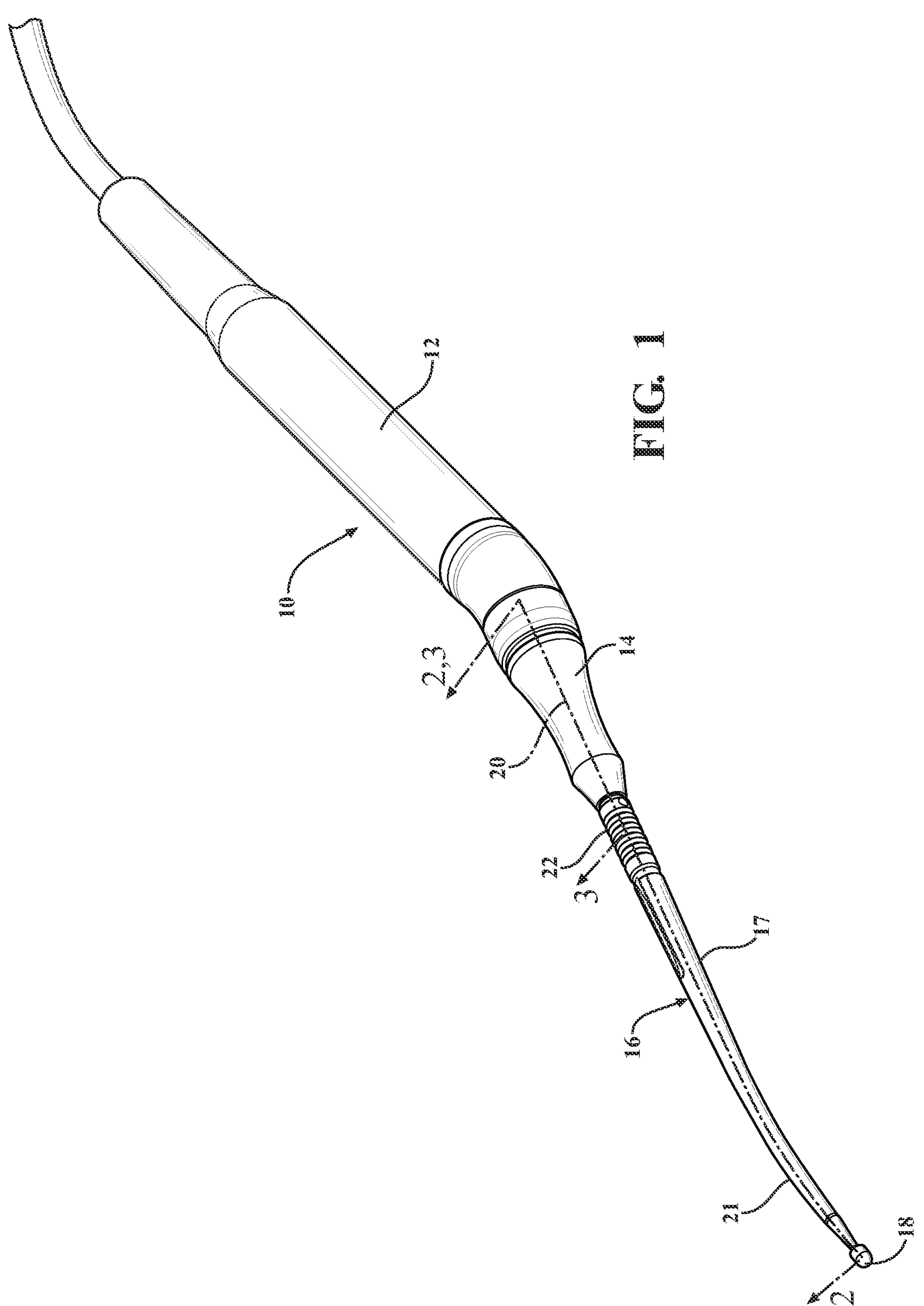
FIG. 1 is a perspective view of a surgical handpiece system including a hub coupled to a nose tube assembly.

FIG. 1 depicts a perspective view of a surgical handpiece system 10. The surgical handpiece system 10 includes a motor 12, a hub 14 and a nose tube assembly 16. The motor 12 connects to the hub 14, and the nose tube assembly 16 connects to the motor 12 through the hub 14. The nose tube assembly 16 includes a nose tube 17, a driveshaft 24 (see FIG. 2), and a cutting tool 18 coupled to the driveshaft 24. The motor 12 is configured to provide torque through the hub 14 to the nose tube assembly 16. Specifically, the motor 12 transfers torque through the hub 14 to the driveshaft 24 of the nose tube assembly 16 that rotates a cutting tool 18 of the nose tube assembly 16 disposed at a distal end 21 of the nose tube assembly 16. The motor 12 is configured to transfer torque through the hub 14 and the nose tube assembly 16 to the cutting tool 18. In some configurations, the motor 12 is configured to rotate the cutting tool 18 at speeds greater than 50,000 revolutions per minute. The high-speed torque transfer from the motor 12 to the cutting tool 18 allows the nose tube assembly 16 to accurately and efficiently abrade a nasal passage, for example. The nose tube assembly 16 may also be adapted for spinal, neuro, and endoscopic applications.

The hub 14 may include a variety of different configurations. The hub 14 may be straight, or curved depending on use. For example, in a curved configuration, the hub 14 may define a twenty-degree seamless curve away from a horizontal axis 20 of the hub 14, or the hub 14 may define a straight length along the horizontal axis 20. Additionally, the nose tube assembly 16 may also be curved or straight depending on application of the nose tube assembly 16. More specifically, the nose tube 17 may be curved or straight. For example, the nose tube assembly 16 may include a bend at a proximal end 22, or may include a bend at the distal end 21 of the nose tube assembly 16. Transnasal applications of the nose tube assembly 16 may employ a bend at the distal end 21, and spinal applications of the nose tube assembly 16 may employ a bend at the proximal end 22 of the nose tube assembly 16. Bushings (not shown) align the driveshaft 24 within a lumen 26 (see FIG. 2) of the nose tube 17 so that the driveshaft 24 does not contact an inner surface of the nose tube 17. This allows the driveshaft 24 to rotate independently of the nose tube 17 when the motor 12 transfers torque through the driveshaft 24.

Shown in FIG. 1 is a curved hub 14. The curved hub 14 differs from the straight hub based on the desired surgical application of the surgical handpiece system 10. As noted above, the degree to which the hub 14 and/or the nose tube assembly 16 may be bent may be influenced by surgical application. It is contemplated that the hub 14 and/or the nose tube assembly 16 may be straight and not employ any bends. Specifically, the curved hub 14 may include a plurality of ball bearings (not shown) or other torque transfer mechanisms used to support rotatable components that allow the curved hub 14 to transfer torque to the nose tube assembly 16. The bearings provide alignment of shafts (not shown) interconnected by a gear set (not shown) to transfer torque from the motor 12 through the hub 14 and to the nose tube assembly 16.

As stated above, the hub 14 attaches to the motor 12. The hub 14 may include features that aid in aligning and locking the hub 14 to the motor 12 of the surgical handpiece system 10. For example, the hub 14 may include a visual indicator such as a dot (not shown) that corresponds to another dot (not shown) on the motor 12 such that alignment between the dots allows the hub 14 to couple to the motor 12. Additionally, the hub 14 may include an anti-rotation pin (not shown) at the proximal end 22 of the hub 14 to allow specific orientations between the hub 14 and the motor 12. An external c-clip (not shown) as well as an O-ring (not shown) may further aid to establish a secure connection between the hub 14 and the motor 12 such that the motor 12 transfers torque through the hub 14 to the nose tube assembly 16. The hub 14 may also include a knurled portion (not shown). The knurled portion corresponds to a position on the hub 14 where an operator may place a finger to hold the surgical handpiece system 10.

Figures 2, 3:
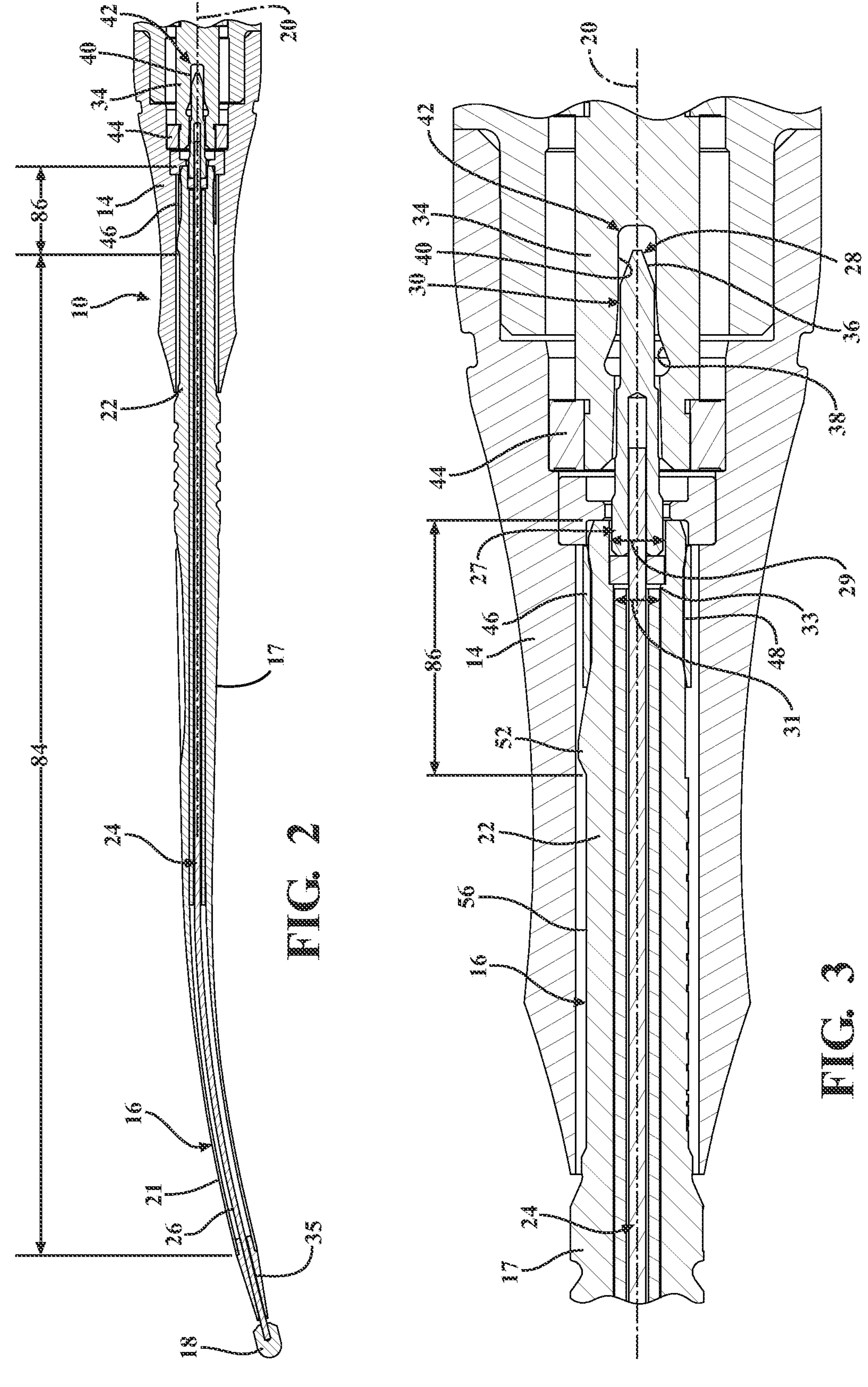
FIG. 2 is a cross-sectional view of the nose tube assembly coupled to the hub taken along lines 2-2 in FIG. 1.
FIG. 3 is a partial, cross-sectional view of a proximal end of the nose tube assembly coupled to the hub taken along lines section 3-3 in FIG. 1.

FIG. 2 depicts a cross-sectional view of the surgical handpiece system 10 taken along lines 2-2 in FIG. 1. Specifically, FIG. 2 shows a cross-section of the nose tube assembly 16 and the hub 14. The motor 12 is not shown in FIG. 2. The nose tube assembly 16 is shown having the driveshaft 24 extending through the lumen 26 defined in the nose tube 17. The driveshaft 24 extends into the hub 14 and the hub 14 is configured to transfer torque from the motor 12 to the driveshaft 24. The driveshaft 24 is shown as extending between and beyond the proximal and distal ends 22, 21 of the nose tube assembly 16.

As shown in FIGS. 2 and 3, the driveshaft 24 is at least partially disposed within the lumen 26. The driveshaft 24 also includes an alignment portion 28. The alignment portion 28 is configured to align a drive portion 30 of the driveshaft 24 into an orientation to engage a rotatable drive chuck 34 disposed within the hub 14. The rotatable drive chuck 34 is placed into alignment with the driveshaft 24 of the nose tube assembly 16 with the hub 14 to transfer torque through the driveshaft 24 from the motor 12. As will be described in more detail below, the alignment portion 28 of the driveshaft 24 is disposed at the proximal end 22 of the nose tube assembly 16. To align the driveshaft 24 with the hub 14, the rotatable drive chuck 34 engages a leading edge 36 of the alignment portion 28 of the driveshaft 24 as the nose tube assembly 16 is urged towards the hub 14. Specifically, the alignment portion 28 defines one or more leading edges 36 to engage one or more ramped surfaces 38 of the rotatable drive chuck 34 to align the drive portion 30 of the driveshaft 24 in the rotatable drive chuck 34. As described in more detail further below, the configuration of the ramped surfaces 38 of the rotatable drive chuck 34 and the leading edges 36 of the alignment portion 28 permits the driveshaft 24 to be self-aligning. Said differently, when the nose tube assembly 16 is urged toward the hub 14, the leading edge 36 of the alignment portion 28 engages the ramped surface of the rotatable drive chuck 30 to rotate the driveshaft 24. This engagement and continued urging of the nose tube assembly 16 toward the hub 14 will rotate the driveshaft 24 to an orientation where the drive portion 30 engages the rotatable drive chuck 34 to permit torque transfer between the driveshaft 24 and the rotatable drive chuck 34. Regardless of the initial radial orientation of the alignment portion 28, the configuration of the ramped surfaces 38 of the rotatable drive chuck 34 and the leading edges 36 of the alignment portion 28 will ensure that the drive portion 30 of the driveshaft 24 is in the orientation to engage the rotatable drive chuck 34 when the nose tube assembly 16 is urged toward the hub 14. The self-aligning feature is beneficial in certain embodiments because the driveshaft 24 is not visible when the nose tube assembly 16 is coupled to the hub 14 and because the driveshaft 24 is not axially movable within the nose tube assembly 16. Thus, a user grasps the outer surface of the nose tube 17 and urges it towards the hub 14. Through axial movement alone, the engagement between the alignment portion 28 of the driveshaft 24 and the rotatable drive chuck 34 results in rotation of the driveshaft 24 without requiring the user to spin the cutting tool 18 of the nose tube assembly 16 to obtain a proper orientation of the drive portion 30 to the rotatable drive chuck 34.

Proper alignment between the hub 14 and the driveshaft 24 may be indicated by tactile feedback. More specifically, when the leading edge 36 of the alignment portion 28 engages the ramped surface 38 of the rotatable drive chuck 34, haptic feedback such as, for example, vibrations from contact between the leading edge 36 and the ramped surface 38, may be felt through the surgical handpiece system 10. The haptic feedback may be indicative of proper alignment between the nose tube assembly 16, the hub 14, and the motor 12.

As shown in FIG. 3, once aligned to a proper orientation, the drive portion 30 of the driveshaft 24 mates with flat surfaces 40 within a drive chamber 42 of the rotatable drive chuck 34. This allows torque to transfer from the motor 12 through the hub 14 to the driveshaft 24. Stated differently, the motor 12 transfers torque through the hub 14 once the drive portion 30 aligns with the flat surface 40 in the drive chamber 42 of the rotatable drive chuck 34, in which the rotatable drive chuck 34 rotates independently from the hub 14. Bearings 44 disposed within the hub 14 aid to align the driveshaft 24 and rotatable drive chuck 34 along the horizontal axis 20 of the surgical handpiece system 10. Therefore, the bearings 44 allow for efficient torque transfer along the horizontal axis 20 by aligning the rotatable drive chuck 34 and driveshaft 24 within the hub 14, and nose tube assembly 16, respectively.

FIG. 3 depicts a partial, cross-sectional view of the driveshaft 24 disposed within the hub 14 taken along lines 3-3 shown in FIG. 1. Specifically, FIG. 3 depicts the drive portion 30 of the driveshaft 24 aligned within the drive chamber 42 of the rotatable drive chuck 34. Bearings 44 are shown engaging the driveshaft 24 and rotatable drive chuck 34 to align the driveshaft 24 and rotatable drive chuck 34 along the horizontal axis 20, and allow the driveshaft 24 and rotatable drive chuck 34 to rotate independently of the hub 14. Independent rotation of the driveshaft 24 and rotatable drive chuck 34 relative to the hub 14 allows the motor 12 to transfer torque through the hub 14 to the cutting tool 18, such as a bur.

Referring again to FIG. 3, the nose tube 17 of the nose tube assembly 16 defines a recess 48 disposed at the proximal end 22 of the nose tube 17, and adjacent the bearings 44 when the nose tube assembly 16 is coupled to the hub 14. Specifically, the nose tube 17 has an outer surface 56 that defines the recess 48 for receiving a biasing member 46, such as a c-clip, to constrain a depth of the nose tube assembly 16 relative to the surgical handpiece system 10. The biasing member 46 is held axially in place using the hub 14. When the nose tube assembly 16 is inserted into the hub 14, the biasing member 46 expands as the nose tube assembly 16 is inserted such that the biasing member 46 then seats within the recess 48 when the nose tube assembly 16 is fully inserted into the hub 14.

The biasing member 46 is disposed in the recess 48 to hold the nose tube assembly 16 in place along the horizontal axis 20 during use of the surgical handpiece system 10. The recess 48, therefore, may also be referred to as a retention feature 48, in which the biasing member 46 is disposed in the retention feature 48 to maintain axial alignment of the nose tube assembly 16 and the driveshaft 24 relative to the hub 14 during use of the surgical handpiece system 10. In other words, as the nose tube assembly 16 is pushed into the hub 14, the biasing member 46 is opened and grabs onto the recess 48. The biasing member 46 may be referred to as a retention element as the biasing member 46 serves to retain the depth of the nose tube assembly 16 relative to the hub 14 by engaging the retention feature. The biasing member 46 prevents axial movement of nose tube assembly 16 relative to the hub 14. More specifically, the biasing member 46 prevents the nose tube assembly 16 from inadvertently separating from the hub 14 when the biasing member 46 engages the recess 48. The engagement between the biasing member 46 and the recess 48 may be overcome in response to the user applying a force (e.g., by pulling) sufficient to expand the biasing member 46 out of the recess 48 to separate the nose tube assembly 16 from the hub 14.

As described above, the biasing member 46 aids to constrain the nose tube assembly 16 along the horizontal axis 20 relative to the hub 14. As shown in FIG. 3, the recess 48 may define a beveled edge 50 that may be positioned adjacent to a projection 52 of the nose tube 17 extending radially away from the lumen 26 of the nose tube 17 such that the biasing member 46 abuts the projection 52. The beveled edge 50 of the recess 48 may reduce the force required by the user to remove the nose tube assembly 16 from the hub 14.

As shown in FIG. 3, the driveshaft 24 includes a retention portion 27 disposed distal the alignment portion 28 and the drive portion 30 of the driveshaft 24. The retention portion 27 of the driveshaft 24 may be disposed within the lumen 26 of the nose tube 17. Specifically, the retention portion 27 is configured to extend partially into the nose tube assembly 16 and abut a shelf 33 of the internal surface of the nose tube 17 defining the lumen 26 to constrain the driveshaft 24 relative to the nose tube 17. In some configurations, such as one illustrated in FIG. 3, a bearing may be interposed between the shelf 33 and the retention portion 27 of the driveshaft 24. The retention portion 27 defines a diameter 29 being greater than a diameter 31 of the lumen 26 to allow the retention portion 27 to constrain the driveshaft 24 relative to the nose tube assembly 16. This configuration prevents the driveshaft 24 from being removed axially from the nose tube 17 in a distal direction. In one configuration, the relative diameter of the cutting tool 18 in relation to the lumen 26 and/or a distal bushing 35 (see FIG. 2) coupled to the distal end 21 of the nose tube 17 prevents the driveshaft 24 from being removed axially from the nose tube 17 in a proximal direction.

Figure 4:
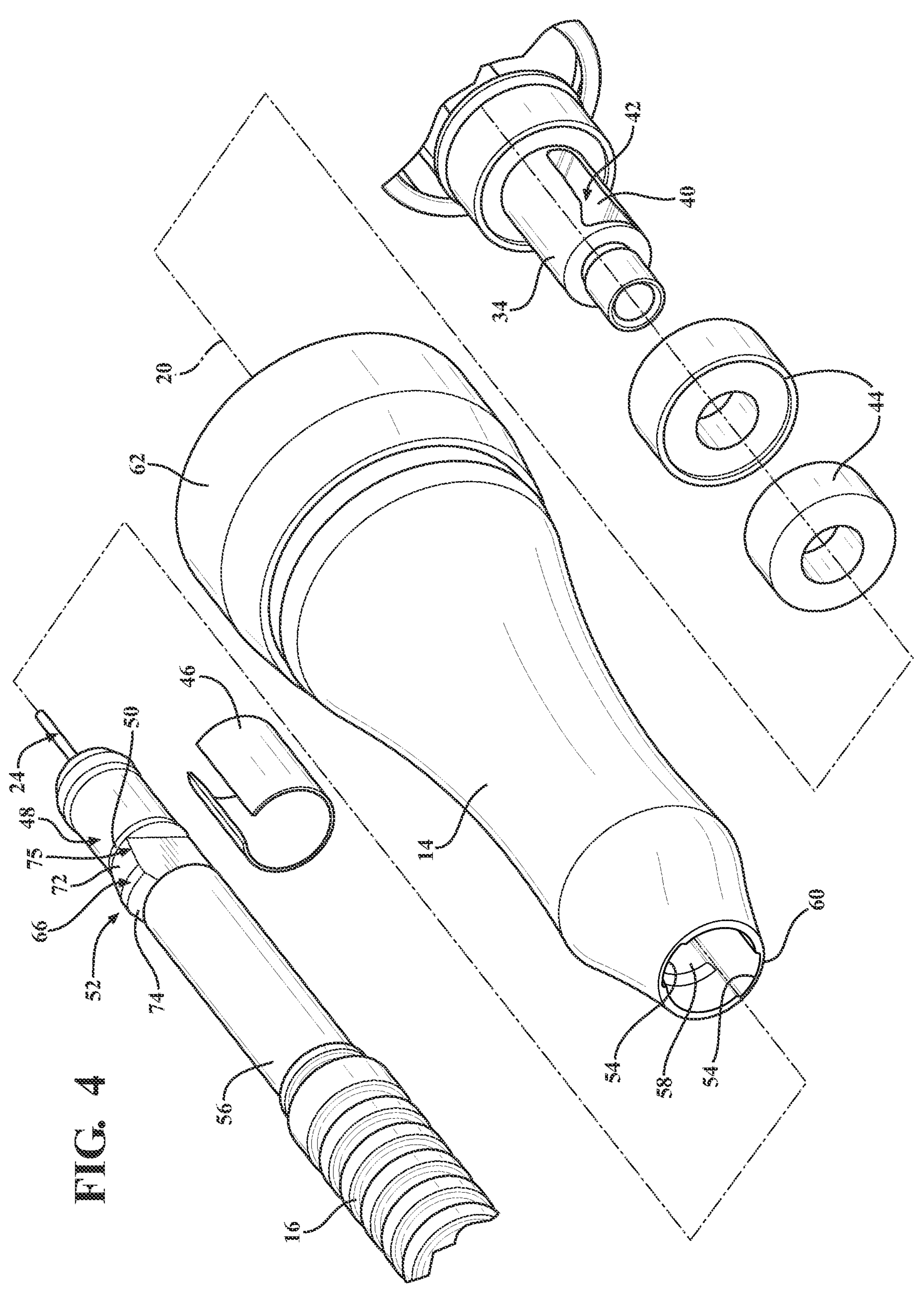
FIG. 4 is an exploded, perspective view of the proximal end of the nose tube assembly, the hub, and the surgical handpiece.
Figures 5, 6:
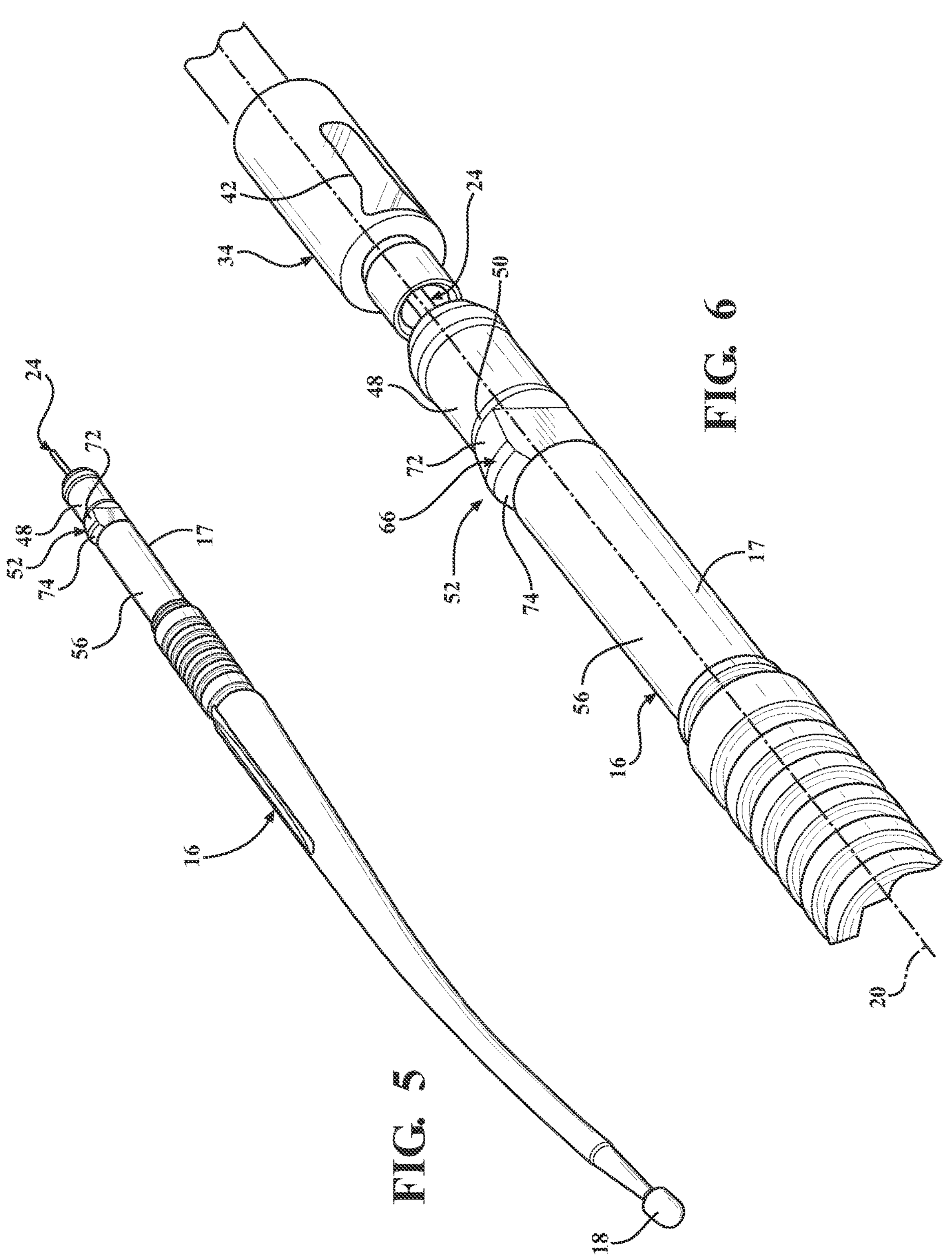
FIG. 5 is a perspective view of a portion of the nose tube assembly.
FIG. 6 is a perspective view of a portion of the nose tube assembly being positioned for insertion into the collet of the hub.

Referring to FIGS. 4-6, partial, perspective views of the nose tube assembly 16 and the rotatable drive chuck 34 are shown. FIG. 4 depicts a partial, perspective, exploded view of the nose tube assembly 16 and the hub 14 of the surgical handpiece system 10. FIG. 4 is shown as exploded along the horizontal axis 20, in which the nose tube assembly 16 and the hub 14 are spaced along the horizontal axis 20. Specifically, FIG. 4 depicts an exploded, perspective view of the nose tube assembly 16 having the projection 52 that extends radially from the surface 56. FIG. 5 depicts a partial perspective view of the nose tube assembly 16 detached from the hub 14. FIG. 6 depicts a partial perspective view of the nose tube assembly 16 defining the recess 48 and the projection 52 on the surface 56 and the rotatable drive chuck 34.

Referring to FIG. 4, the hub 14 has a proximal end 62 and a distal end 60 opposite the proximal end 62. The hub 14 has an internal surface defining a bore 58 extending from the distal end 60 to the proximal end 62. The internal surface also defines a channel 54 in communication with the bore 58 extending from the distal end 60 toward the proximal end 62. The projection 52 of the nose tube 17 is adapted to radially align the nose tube 17 during insertion of the nose tube assembly 16 into the bore 58 of the hub 14. In this way, the projection 52 acts as a radial alignment feature 52 of the nose tube 17. Stated differently, the projection 52 acts as a keyed, alignment feature 52, in which the projection 52 fits into the channel 54 defined in the hub 14. The channel 54 is sized to accommodate the projection 52 such that radial movement of the nose tube 17 when the channel 54 receives the projection 52 is mitigated. Mitigation of this radial movement permits the nose tube assembly 16 to couple to the hub 14 with precision. In this way, the projection 52 slides within the channel 54 to radially align the nose tube 17 relative to the hub 14. There may be two channels 54 and two projections 52, the channels 54 and projections 52 diametrically spaced from one another across the longitudinal axis. In another configuration, there may be two channels 54 and one projection 52 such that the hub 14 permits the nose tube assembly 16 to be coupled to the hub 14 in two different orientations. Such a configuration may be advantageous when the hub 14 and/or the nose tube assembly 16 employs a bend as described above.

As stated, the projection 52 extends radially from the nose tube 17. Specifically, the projection 52 extends vertically from a surface 56 of the nose tube 17. Extending from the surface 56 of the nose tube 17 allows the projection 52 to engage the channel 54 defined in the hub 14 such that radial movement of the projection 52 in the channel 54, for example, from rotating the nose tube 17 relative to the hub 14, is prevented. The engagement of the projection 52 in the channel 54 also serves to grossly align the drive portion 30 of the driveshaft 24 in the drive chamber 42 of the rotatable drive chuck 34. In this way, the projection 52 provides efficient and accurate alignment.

The projection 52 extends from the surface 56 of the nose tube 17 to a peak 66. The peak 66 defines a height of the projection 52. The height of the projection 52 may be based on dimensions of the hub 14. The peak 66 of the projection 52 may be formed from at least one, first, slanted surface 72. As will be described in more detail, the projection 52 may also be formed from two, first and second, slanted surfaces 72, 74. The peak 66 may extend from the first slanted surface 72 to the second slanted surface 74.

The first slanted surface 72 may extend from the beveled edge 50 of the recess 48 to the peak 66 of the projection 52. The second slanted surface 74 may be disposed along the alignment portion 28 of the driveshaft 24, and extend to the peak 66 of the projection 52. The first and second slanted surfaces 72, 74 may also define opposite inclinations such that the first and second slanted surfaces 72, 74 culminate at the peak 66 of the projection 52. Angles that form the inclination of the first and second slanted surfaces 72, 74 may vary, or be equal based on an optimal extension and operation of the projection 52 as the projection 52 slides in the channel 54. Stated differently, the peak 66 may extend between the first and second slanted surfaces 72, 74 to interconnect the first and second surfaces 72, 74, which defines the height of the projection 52. The first and second slanted surfaces 72, 74 also aid to allow the projection 52 to slide into the channel 54 in the hub 14. The first and second slanted surfaces 72, 74 provide ease of assembly by reducing frictional forces as the projection 52 slides through the channel 54. Additionally, the peak 66 may define a radius between the first and second slanted surfaces 72, 74. For example, the peak 66 may be rounded between the first and second slanted surfaces 72, 74. The radius of the peak 66 may be determined based on optimal sliding parameters of the projection 52 in the channel 54. Therefore, the radius of the peak 66 may be formed to fit within the channel 54 defined in the hub 14. Other shapes of the projection 52 are also contemplated.

As previously described, the projection 52 is disposed adjacent to the recess 48. Specifically, in certain configurations, the first slanted surface 72 is formed proximate the beveled edge 50 of the recess 48. Both the retention (shown as the recess) and radial alignment features (shown as the projection) 48, 52 of the nose tube assembly 16 may be disposed adjacent to each other. Since the projection 52 is disposed adjacent the recess 48, the biasing member 46 abuts the projection 52 on the nose tube 17 when the nose tube assembly 16 is coupled to the hub 14. To maintain alignment during insertion, the projection 52 defines the height of the peak 66 relative to the horizontal axis 20 and the recess 48 defines a distance to the horizontal axis 20 being less than the height of the peak 66. The height of the peak 66 being greater than the distance from the biasing member 46 to the horizontal axis 20 allows the projection 52 to adequately engage and slide in the channel 54 formed in the hub 14.

In another configuration, if the recess 48 defined the distance from the horizontal axis 20 as being greater than the height of the peak 66, the peak 66 may not engage the channel 54, and rotational misalignment between the nose tube 17 and the hub 14 may be introduced during use of the surgical handpiece system 10. Therefore, the distance from the recess 48 to the horizontal axis 20 being less than the height of the peak 66 allows the projection 52 to maintain rotational alignment between the nose tube 17 and the hub 14 during use of the surgical handpiece system 10, while subsequently allowing the retention feature 48 to maintain axial alignment of the nose tube assembly 16, and hence the driveshaft 24, with the features of the hub 14.

It may be useful to understand the nose tube 17 in terms of a first region 84 and a second region 86 (see FIGS. 2 and 3). The first region 84 may represent the majority of the length of the nose tube 17, while the second region 86 may be the portion of the nose tube 17 that interacts with the hub 14. In certain configurations, the first region 84 and second region 86 may both be formed from a metallic material, such as stainless steel. The second region 86 may extend monolithically from the first region 84 from a single piece of metal stock. In other words, the nose tube 17, including both the first region 84 and the second region 86 may be formed from a single piece of metal stock. The second region 86 may include the radial alignment feature 52 and an axial retention feature 48 to axially retain the nose tube assembly 16 in the surgical handpiece system 10. The alignment and retention features 52, 48 may be formed from the metallic material that forms the first and second regions 84, 86, and hence the alignment features 52 and the retention features 48 may be machined from the same piece of metal stock that is used to machine the first region 84 of the nose tube 17.

Figure 7:
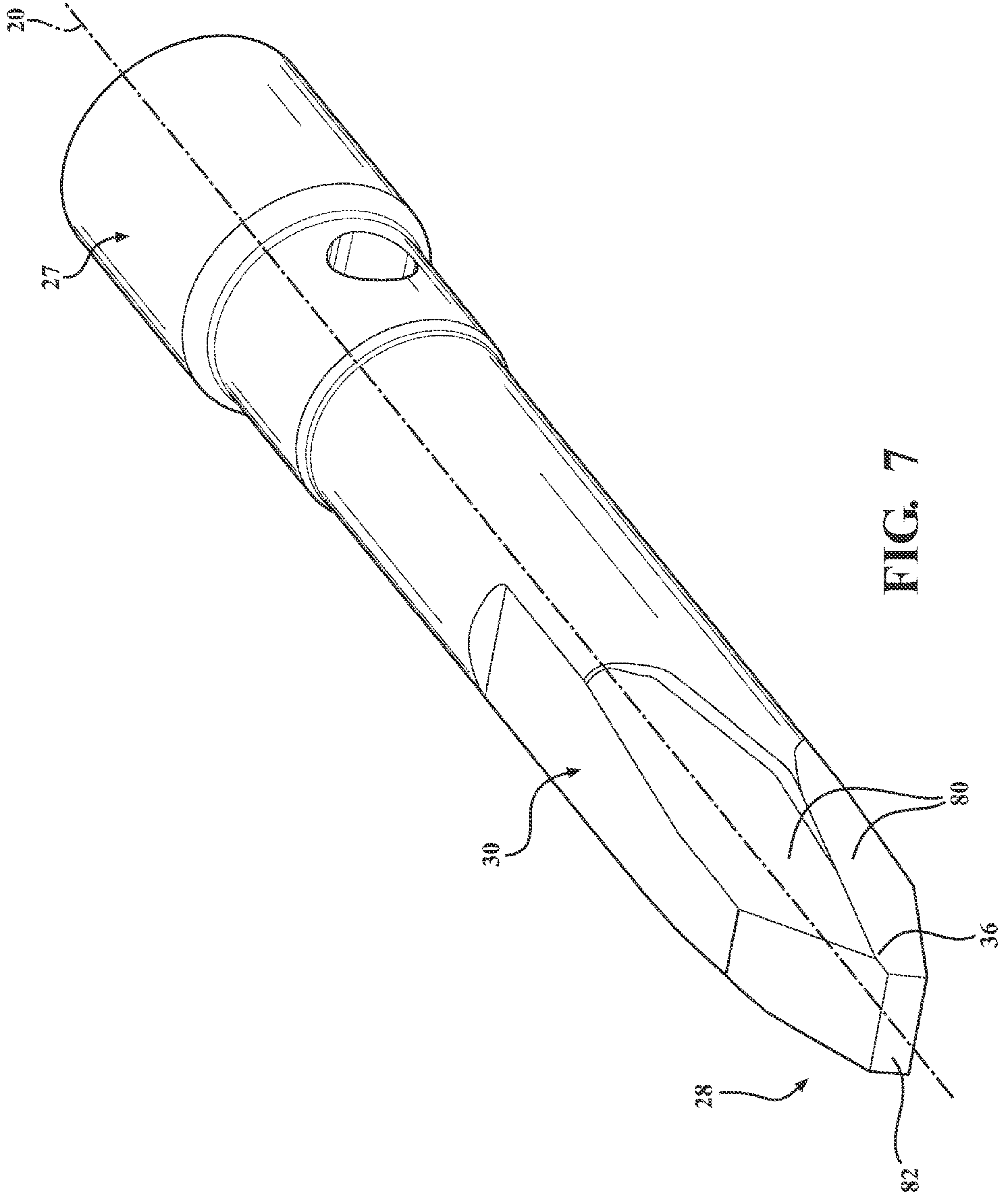
FIG. 7 is a perspective view of a proximal portion of a driveshaft of the nose tube assembly.
Figure 8:
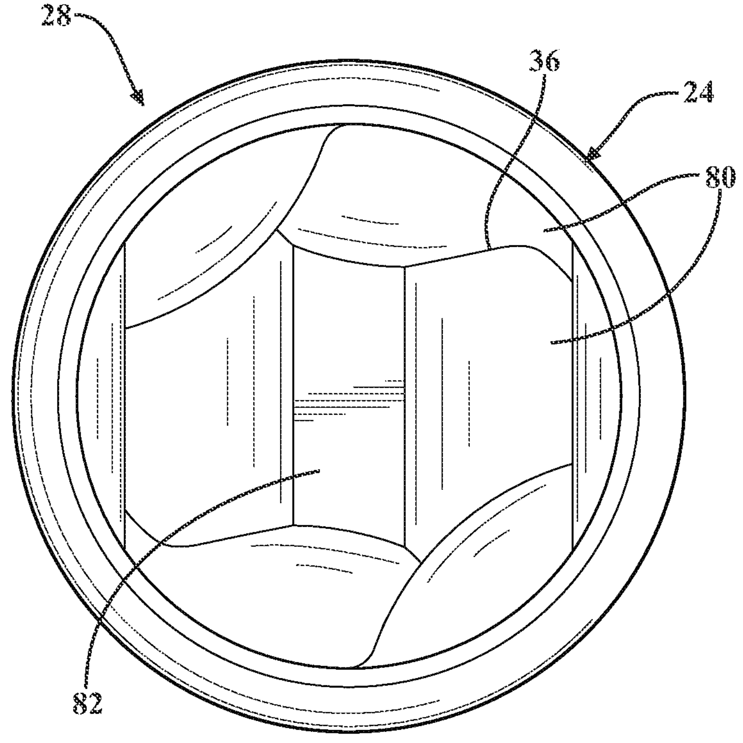
FIG. 8 is a front view of an alignment portion of the driveshaft.

Referring to FIGS. 7 and 8, the proximal portion of the driveshaft 24 is shown. FIG. 7 depicts a perspective view of the alignment portion 28 including the leading edge 36, the retaining portion 27, and the drive portion 30. FIG. 8 depicts a front view of the proximal portion of the driveshaft 24. Specifically, FIG. 8 depicts a front view of the alignment portion 28 of the driveshaft 24.

In one exemplary configuration of assembly, a user grasps the nose tube 17 of the nose tube assembly 16. The user partially inserts the nose tube assembly 16 within the bore 58 of the hub 14. Then the user aligns the projection 52 of the nose tube 17 with the channel 54 of the hub 14 and continues to urge the nose tube assembly 16 toward the hub 14. The engagement between the projection 52 and the channel 54 radially aligns the nose tube 17 to the hub 14. When the proximal end of the nose tube 17 abuts the biasing member 46, the biasing member 46 expands to accommodate the nose tube 17. Continued urging of the nose tube assembly 16 toward the hub 14 results in the biasing member 46 being received by the recess 48 of the nose tube 17. When the recess 48 receives the biasing member 46, the nose tube 17 and the rest of the nose tube assembly 16 are axially retained relative to the hub 14.

Before the recess 48 receives the biasing member 46, the leading edge 36 of the alignment portion 28 of the driveshaft 24 abuts the ramped surface 38 of the rotatable drive chuck 34 to cam the driveshaft 24, and thus the drive portion 30 of the driveshaft 24, toward the orientation where the drive portion 30 of the driveshaft 24 engages the rotatable drive chuck 34. When the recess 48 receives the biasing member 46, the driveshaft 24 has been cammed into the orientation with the drive portion 30 received in the drive chamber 42 of the rotatable drive chuck 34 and the drive portion 30 abutting the flat surface 40 of the rotatable drive chuck 34 to receive torque from and rotate with the rotatable drive chuck 34. Depending on an initial radial orientation of the driveshaft 24 when the nose tube assembly 16 is first introduced into the hub 14 (i.e., before camming), the leading edge 36 of the alignment portion 28 may first contact the ramped surface 38 of the rotatable drive chuck 34 at different axial positions of the nose tube 17 relative to the hub 14. It is contemplated that where the initial radial orientation of the driveshaft 24 is already in the orientation required for the drive portion 30 of the driveshaft 24 to be received in the drive chamber 42 and engage the rotatable drive chuck 34, the leading edge 36 of the alignment portion 28 would not contact the ramped surface 38 of the rotatable drive chuck 34.

The axial position of the driveshaft 24 relative to the rotatable drive chuck 34 is maintained by the axial retention of the nose tube 17 to the hub 14 via the biasing member 46 and the recess 48. In other words, because the driveshaft 24 is axially retained relative to the nose tube 17, the axial position of the driveshaft 24 relative to the hub 14 and rotatable drive chuck 34 is tied to the axial position of the nose tube 17 relative to the hub 14 and the rotatable drive chuck 34. The nose tube 17 is retained by the biasing member 46 until the user pulls the nose tube assembly 16 relative to the hub 14 with sufficient force to overcome the biasing member 46 by expanding the biasing member 46.

As previously described, the alignment portion 28 of the driveshaft 24 defines the leading edge 36 that aids to align the drive portion 30 of the driveshaft 24 in the drive chamber 42 of the rotatable drive chuck 34. When the nose tube assembly 16 is inserted into the bore 58 of the hub 14, the leading edge 36 engages the ramped surface 38 of the drive chamber 42 in the rotatable drive chuck 34 to align the drive portion 30 of the driveshaft 24 in the drive chamber 42 of the rotatable drive chuck 34. The leading edge 36 engages the ramped surface 38 to translate an insertion force into a rotational force to provide alignment between the drive portion 30 of the driveshaft 24 and the rotatable drive chuck 34. While described as a single leading edge 36, the alignment portion 28 of the driveshaft 24 may include one or more leading edges 36.

FIG. 6 depicts the leading edges 36 as being defined between at least two curved surfaces 80 defined on the alignment portion 28 of the driveshaft 24. The curved surfaces 80 that interconnect to define the leading edges 36. The leading edges may be asymmetrical across the horizontal axis 20. The curved surfaces 80 connect to form a tip 82 of the alignment portion 28. The tip 82, as shown in FIGS. 7 and 8, resembles a parallelogram. As described previously, the rotatable drive chuck 34 rotates independently of the hub 14. Upon insertion of the projection 52 into the channel 54, the alignment portion 28 engages the ramped surface 38 of the rotatable drive chuck 34 to alignment the drive portion 30 in the drive chamber 42. Specifically, the leading edge 36 contacts the ramped surface 38 to cause a cam rotation of the driveshaft 24 to ensure proper alignment of the drive portion 30 in the drive chamber 42. Therefore, the leading edges 36 further aid to align the drive portion 30 of the driveshaft 24 with the flat surface 40 in the drive chamber 42 to accurately transfer torque from the motor 12 to the cutting tool 18 disposed at the distal end 21 of the nose tube assembly 16.

Referring to FIGS. 9-25, another configuration of the surgical handpiece system 100 is illustrated. It should be appreciated that the configuration of the surgical handpiece system 10 described above may include similar elements to the surgical handpiece system 100 described below and vice versa.

Figure 9:
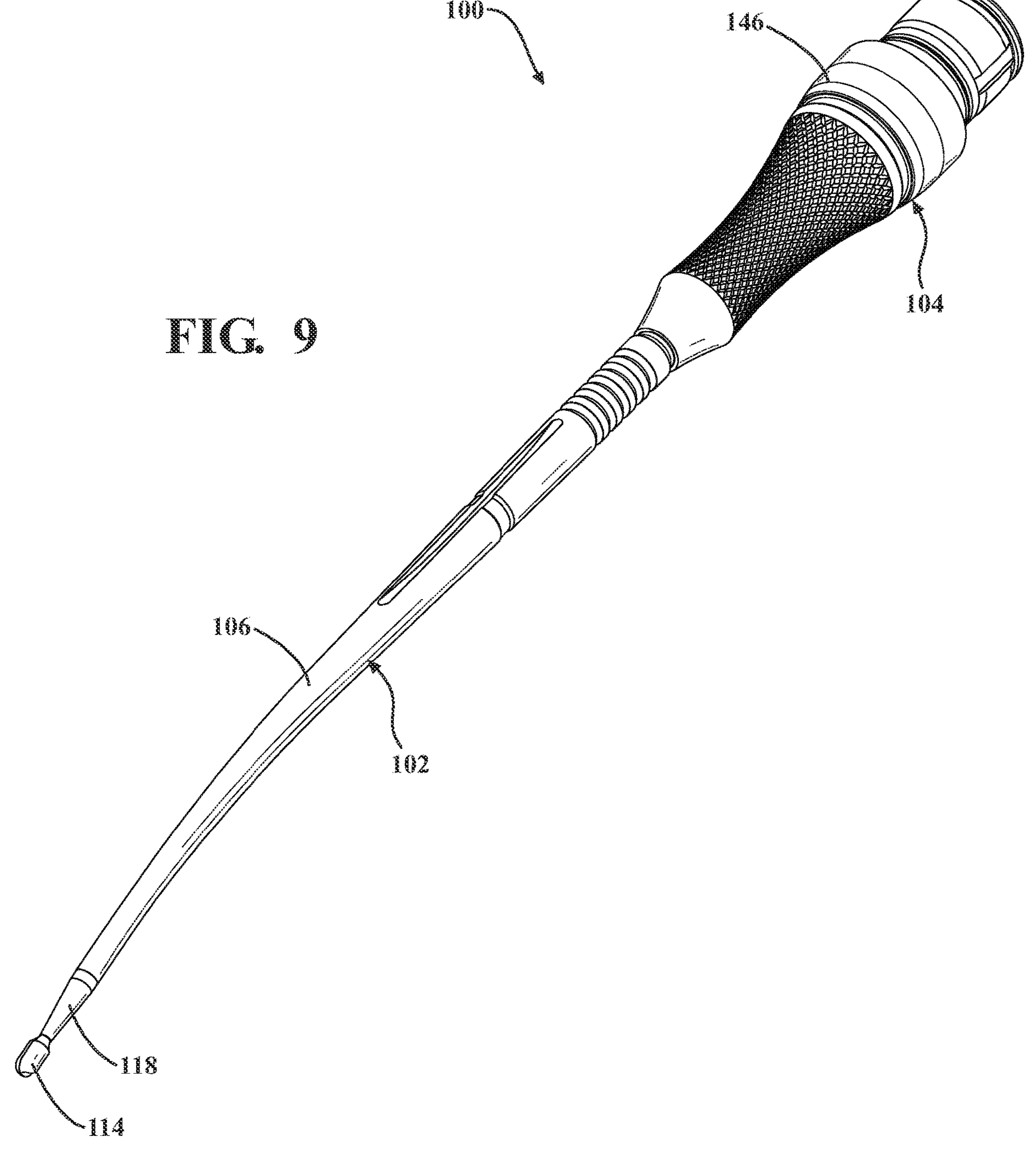
FIG. 9 is a perspective view of another configuration of a surgical handpiece system.
Figure 10:
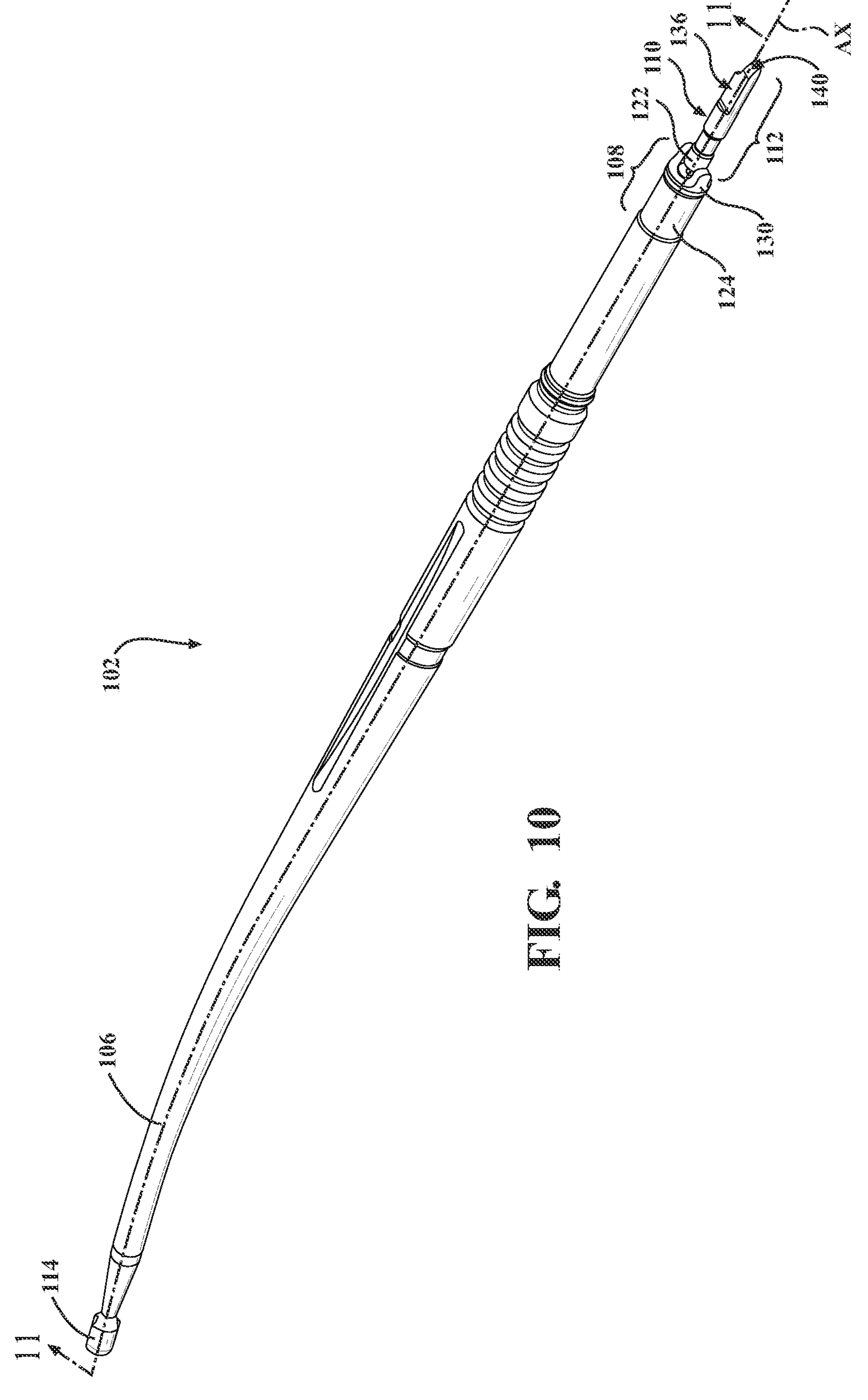
FIG. 10 is a perspective view of a high-speed surgical bur assembly of the surgical handpiece system of FIG. 9.
Figure 14:
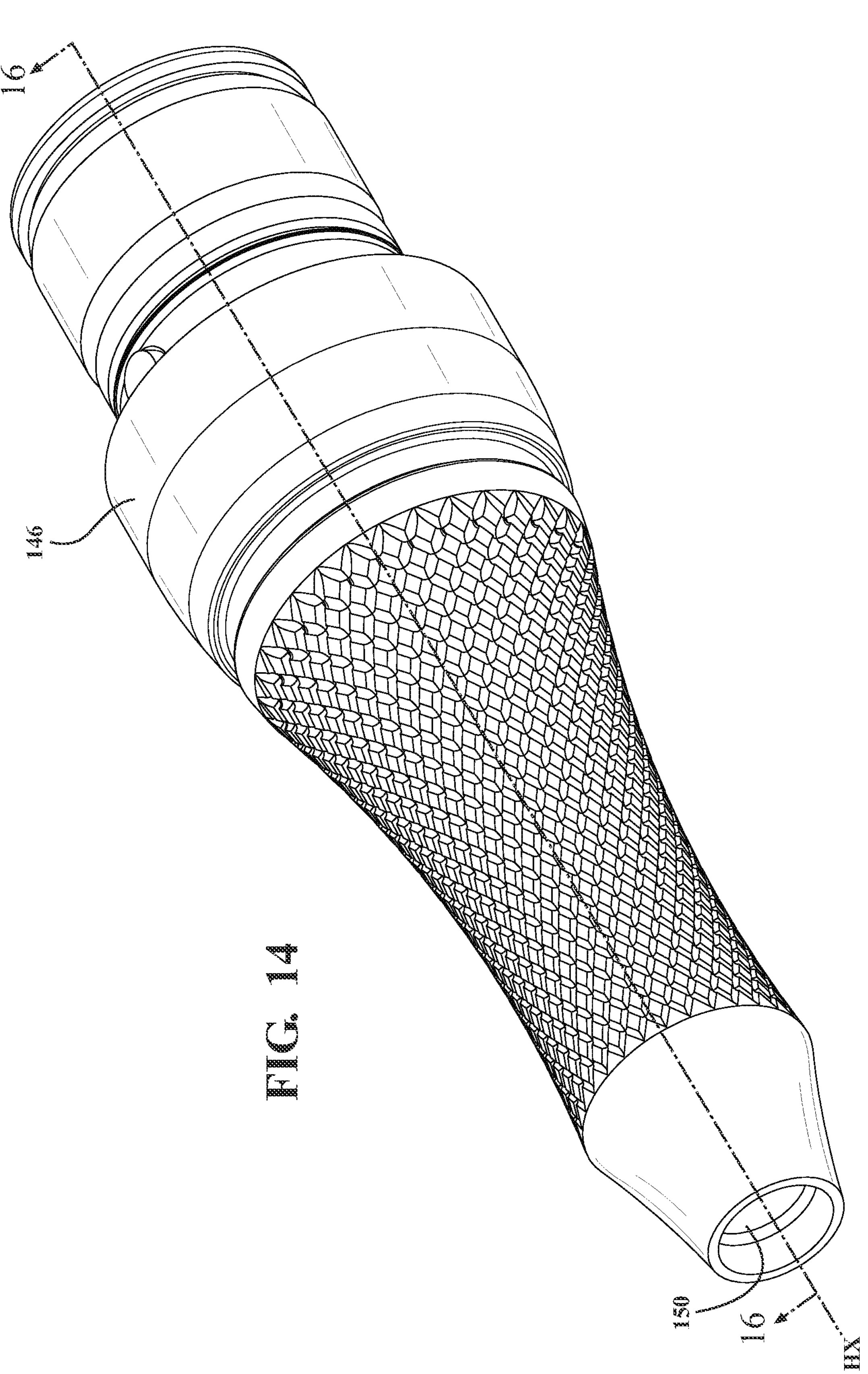
FIG. 14 is a perspective view of a surgical handpiece assembly of the surgical handpiece system of FIG. 9.

As shown in FIG. 9, the surgical handpiece system 100 comprises a high-speed surgical bur assembly 102 (FIG. 10) and a surgical handpiece assembly 104 (FIG. 14). Similarly to the configuration of the surgical handpiece system 10 shown in FIGS. 1-8, the surgical handpiece system 100 may also comprise a motor (not shown) configured to be coupled to the surgical handpiece assembly 104 to provide torque to the surgical handpiece system 100.

Figure 11:
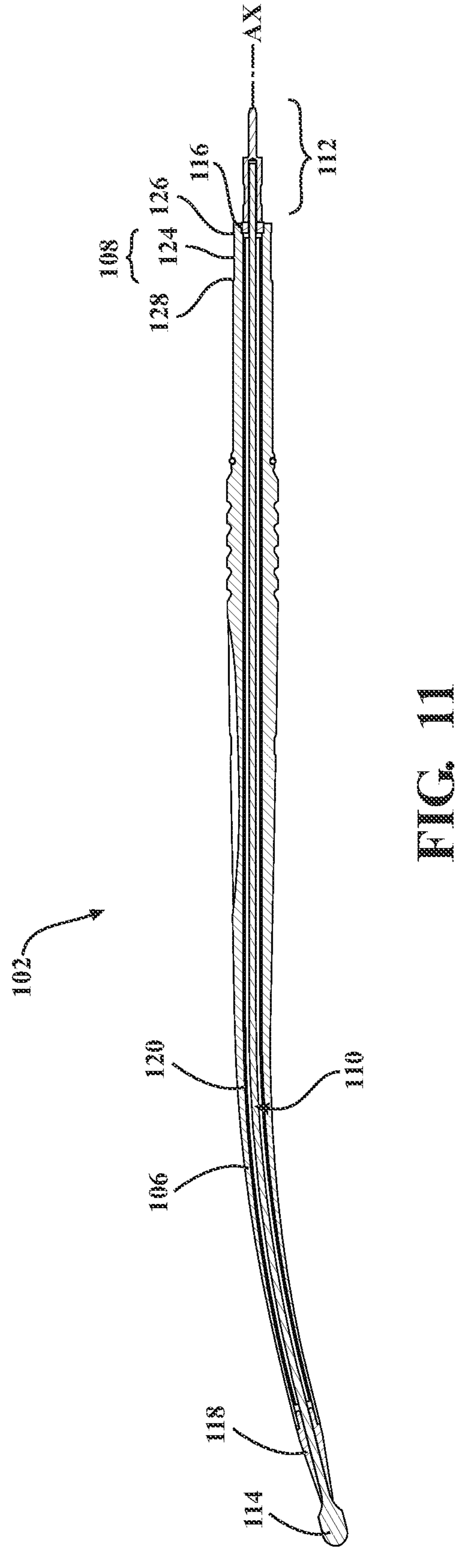
FIG. 11 is a sectional view of the high-speed surgical bur assembly of FIG. 10 taken along lines 11-11 of FIG. 10.

Referring to FIG. 11, a cross-section of one configuration of the high-speed surgical bur assembly 102 is illustrated. The high-speed surgical bur assembly 102 comprises a nose tube 106. The nose tube 106 defines a lumen extending between a proximal end and a distal end of the nose tube 106. At least a proximal portion 108 of the nose tube 106 extends along an axis AX. The nose tube 106 may include a bend such as a distal bend of the nose tube 106 illustrated in FIG. 11 rather than extend axially along an entire length of the nose tube 106. The bend may assist a user in positioning the distal end of the nose tube 106 in certain advantageous positions during surgery.

The high-speed surgical bur assembly 102 further comprises a driveshaft 110 that is at least partially disposed within the lumen of the nose tube 106. The driveshaft 110 is configured to rotate relative to the nose tube 106. A proximal region 112 of the driveshaft 110 is configured to engage the surgical handpiece assembly 104 as described in greater detail further below. The high-speed surgical bur assembly 102 further comprises a cutting tool 114 that is coupled to a distal region of the driveshaft 110. The cutting tool 114 is configured to rotate with the driveshaft 110 relative to the nose tube 106. In one configuration, the cutting tool 114 is a bur. In other configurations, the cutting tool 114 comprises another rotary tool configured to abrade tissue.

The high-speed surgical bur assembly 102 may comprise bushings 116, 118, 120 for facilitating relative rotation between the driveshaft 110 and the nose tube 106. A proximal bushing 116 may be coupled to the nose tube 106 and disposed at least partially within the lumen of the nose tube 106 and around the driveshaft 110. A distal bushing 118 may be coupled to the nose tube 106 and disposed at least partially within the lumen of the nose tube 106 and around the driveshaft 110. A middle bushing 120 may be disposed within the lumen between the proximal and distal bushings 116, 120 to prevent contact between the driveshaft 110 and the nose tube 106 within the lumen of the nose tube 106. In one configuration, the middle bushing 120 is fixed to the nose tube 106. In another configuration, the proximal and distal bushings 116, 118 retain the middle bushing 120 within the lumen of the nose tube 106. In other configurations the middle bushing 120 is retained in the lumen of the nose tube 106 by the bend in the nose tube 106 and corresponding bend of the middle bushing 120. The proximal and distal bushings 116, 118 may also serve as retention features for coupling the driveshaft 110 to the nose tube 106. In one configuration, the proximal region 112 of the driveshaft 110 comprises a retention portion 122 proximal to the proximal bushing 116. The retention portion 122 of the proximal region 112 of the driveshaft 110 has an outer diameter greater than an inner diameter of the proximal bushing 116 to prevent movement of the driveshaft 110 in a distal direction relative to the nose tube 106. The cutting tool 114 may have an outer diameter greater than an inner diameter of the distal bushing 118 to prevent movement of the driveshaft 110 in a proximal direction relative to the nose tube 106. In other configurations, the driveshaft 110 is coupled to the nose tube 106 in another manner to permit relative rotation between the driveshaft 110 and the nose tube 106 and prevent axial movement between the driveshaft 110 and the nose tube 106.

Figure 12:
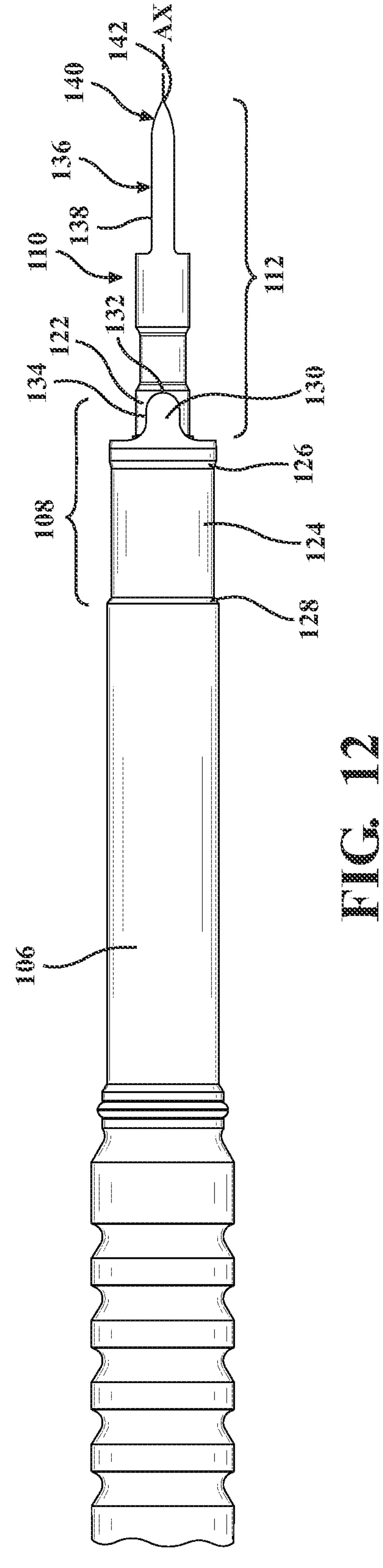
FIG. 12 is an elevation view of a proximal portion of the high-speed surgical bur assembly of FIG. 10.

Referring to FIG. 12, the proximal portion 108 of the nose tube 106 has an outer surface. The outer surface may define a recess 124 for engaging the surgical handpiece assembly 104 to constrain a depth of the nose tube 106 relative to the surgical handpiece assembly 104. The outer surface of the proximal portion 108 of the nose tube 106 may have a proximal shoulder 126 that defines a proximal end of the recess 124 and a distal shoulder 128 that defines a distal end of the recess 124. Either or both proximal and distal shoulders 126, 128 may be tapered. The nose tube 106 may comprise a projection 130 disposed proximal to the recess 124. The projection 130 is configured to constrain a radial orientation of the nose tube 106 relative to the surgical handpiece assembly 104. The projection 130 may extend proximally and generally parallel to the axis AX. The proximal end of the projection 130 may comprise a rounded surface 132. The projection 130 of the proximal portion 108 of the nose tube 106 may include a flat surface 134 that is parallel to the axis AX of the proximal portion 108 of the nose tube 106. The rounded and flat surfaces 132, 134 of the projection 130 may assist engagement between the nose tube 106 and the surgical handpiece assembly 104. Engagement between the nose tube 106 and the surgical handpiece assembly 104 is discussed in greater detail further below. In the configuration illustrated in FIG. 12, the nose tube 106 comprises two projections 130 to constrain the radial orientation of the nose tube 106 relative to the surgical handpiece assembly 104. It is contemplated that a single projection 130 may be used instead to constrain the radial orientation of the nose tube 106 relative to the surgical handpiece assembly 104. It is also contemplated that three or more projections 130 may be employed to constrain the radial orientation of the nose tube 106 relative to the surgical handpiece assembly 104.

Figure 13:
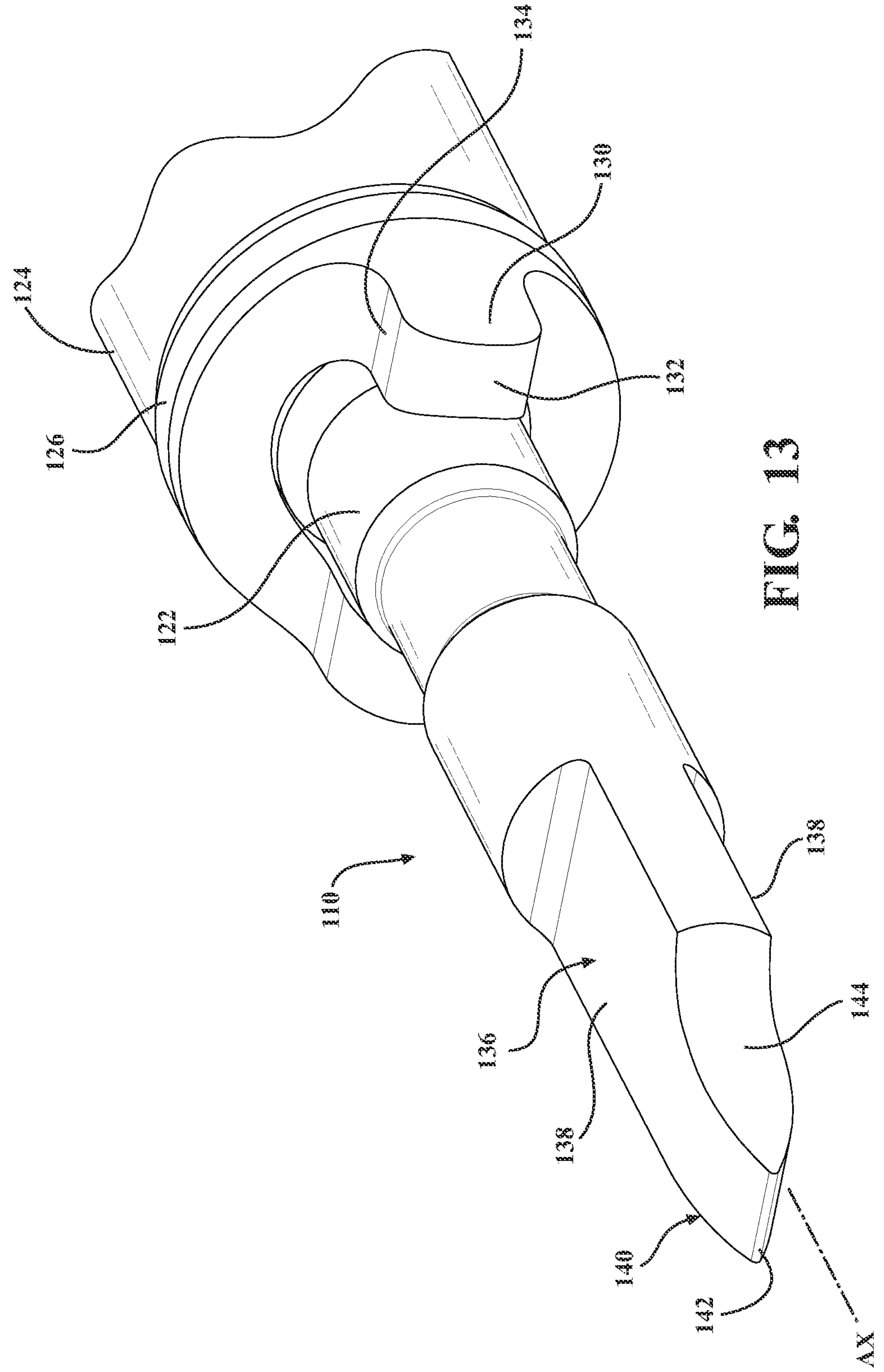
FIG. 13 is a perspective view of a proximal region of a driveshaft of the high-speed surgical bur assembly of FIG. 10.

Referring to FIG. 13, the proximal region 112 of the driveshaft 110 is rotatable about the axis AX of the proximal portion 108 of the nose tube 106. The proximal region 112 of the driveshaft 110 comprises a drive portion 136 proximal to the retention portion 122 for engaging the surgical handpiece assembly 104 in a driving orientation. The drive portion 136 may comprise two or more drive surfaces 138 for engaging the surgical handpiece assembly 104. The drive surfaces 138 may be flat and parallel to the axis AX.

The proximal region 112 of the driveshaft 110 may also comprise an alignment portion 140 proximal to the drive portion 136 of the driveshaft 110. The alignment portion 140 has an outer surface tapering toward the axis AX as the alignment portion 140 extends from the drive portion 136 to a proximal end of the driveshaft 110. The alignment portion 140 is configured to engage the surgical handpiece assembly 104 to align the drive portion 136 to the driving orientation. In the configuration illustrated in FIG. 13, the alignment portion 140 comprises a proximal edge 142 adjacent the proximal end of the proximal region 112 of the driveshaft 110 to engage the surgical handpiece assembly 104. In other configurations, the alignment portion 140 may comprise a flat or rounded surface instead of the proximal edge 142. The alignment portion 140 may define a notch 144 extending distally from the proximal end of the driveshaft 110 for mitigating contact between the alignment portion 140 of the driveshaft 110 and the surgical handpiece assembly 104 during engagement. Mitigating the amount of contact during engagement may reduce potential jamming during engagement resulting from multiple points of contact. In other configurations, the alignment portion 140 may not define the notch 144.

In the configuration illustrated in FIG. 13, the proximal region 112 of the driveshaft 110 is disposed outside of the lumen of the nose tube 106 and proximal the proximal portion 108 of the nose tube 106. In other configurations, the proximal region 112 of the driveshaft 110 may be disposed at least partially within the lumen of the nose tube 106 or distal the proximal portion 108 of the nose tube 106. Engagement between the proximal region 112 of the driveshaft 110 and the surgical handpiece assembly 104 is discussed in greater detail further below.

Figure 27:
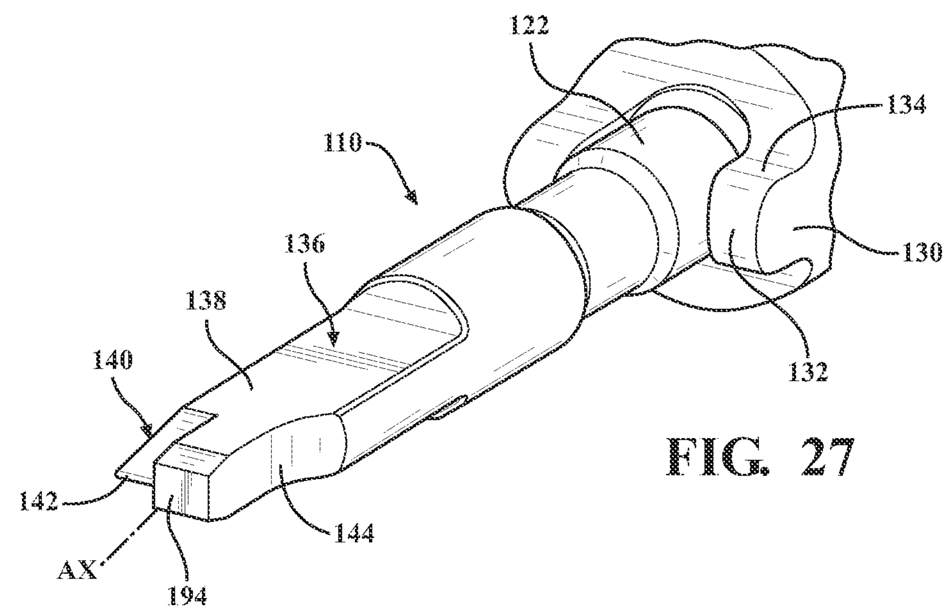
FIG. 27 is a perspective view of another configuration of the driveshaft of the high-speed surgical bur assembly.
Figure 28:
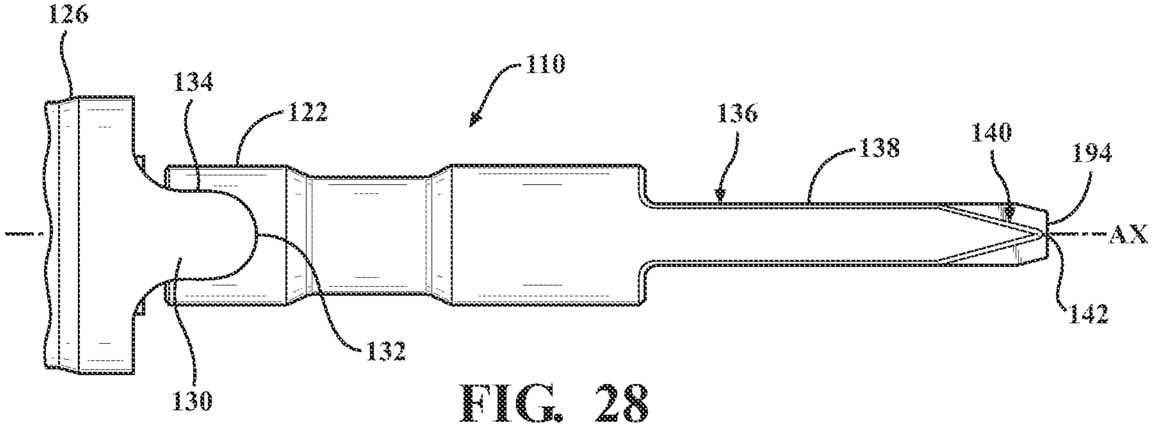
FIG. 28 is an elevation view of the driveshaft of the high-speed surgical bur assembly of FIG. 27.

In another configuration illustrated in FIGS. 27-28, the alignment portion 140 of the driveshaft 110 may comprise a proximal surface 194 disposed proximally of the proximal edge 142 to prevent the proximal edge 142 from engaging the rotatable drive chuck 172 of the surgical handpiece assembly 104 after the drive portion 136 is aligned in the driving orientation. The proximal surface 194 may comprise a planar surface perpendicular to the axis AX. In other configurations, the proximal surface 194 may comprise a rounded surface.

Figure 15:
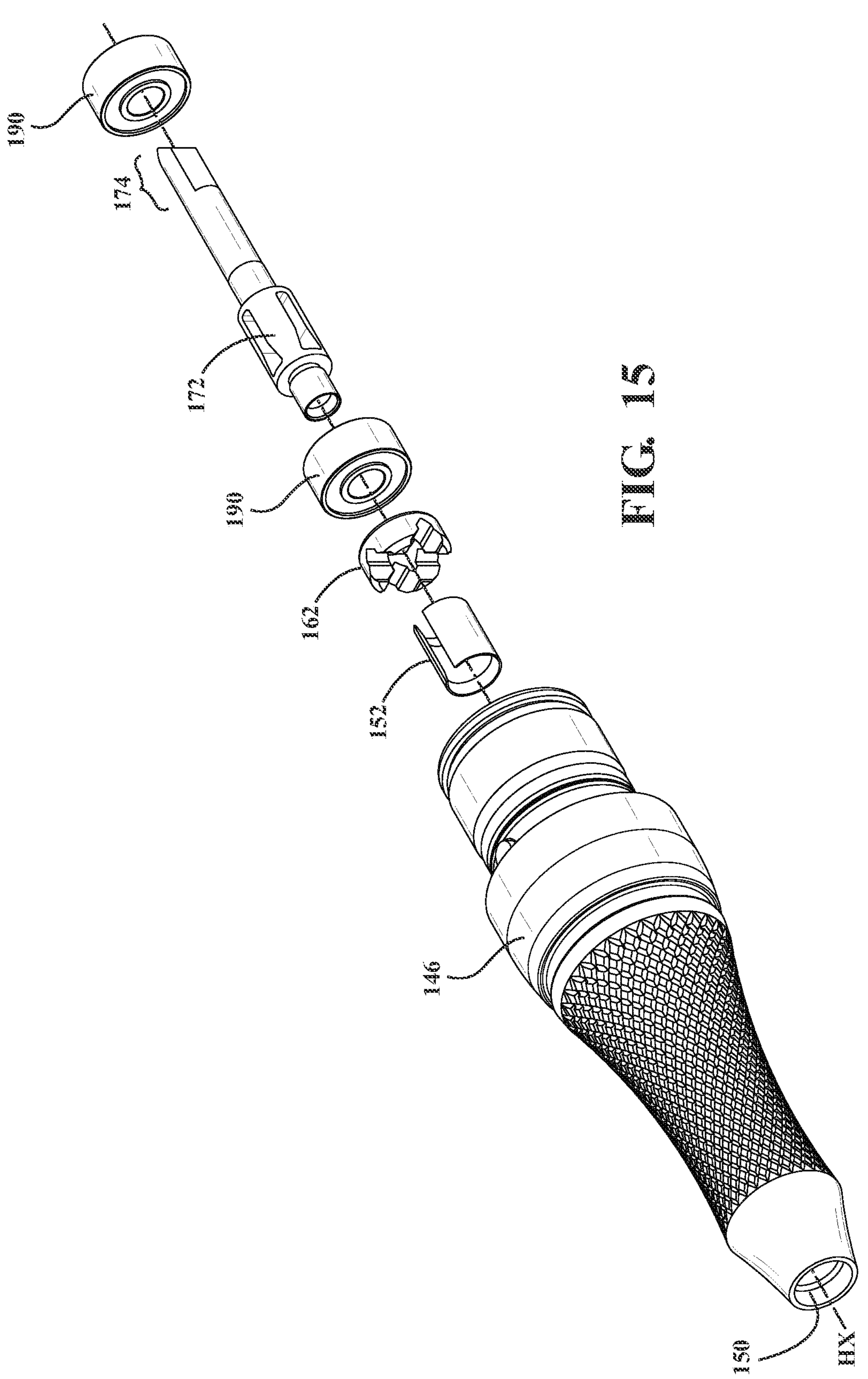
FIG. 15 is an exploded view of the surgical handpiece assembly of FIG. 14.
Figures 16, 17:
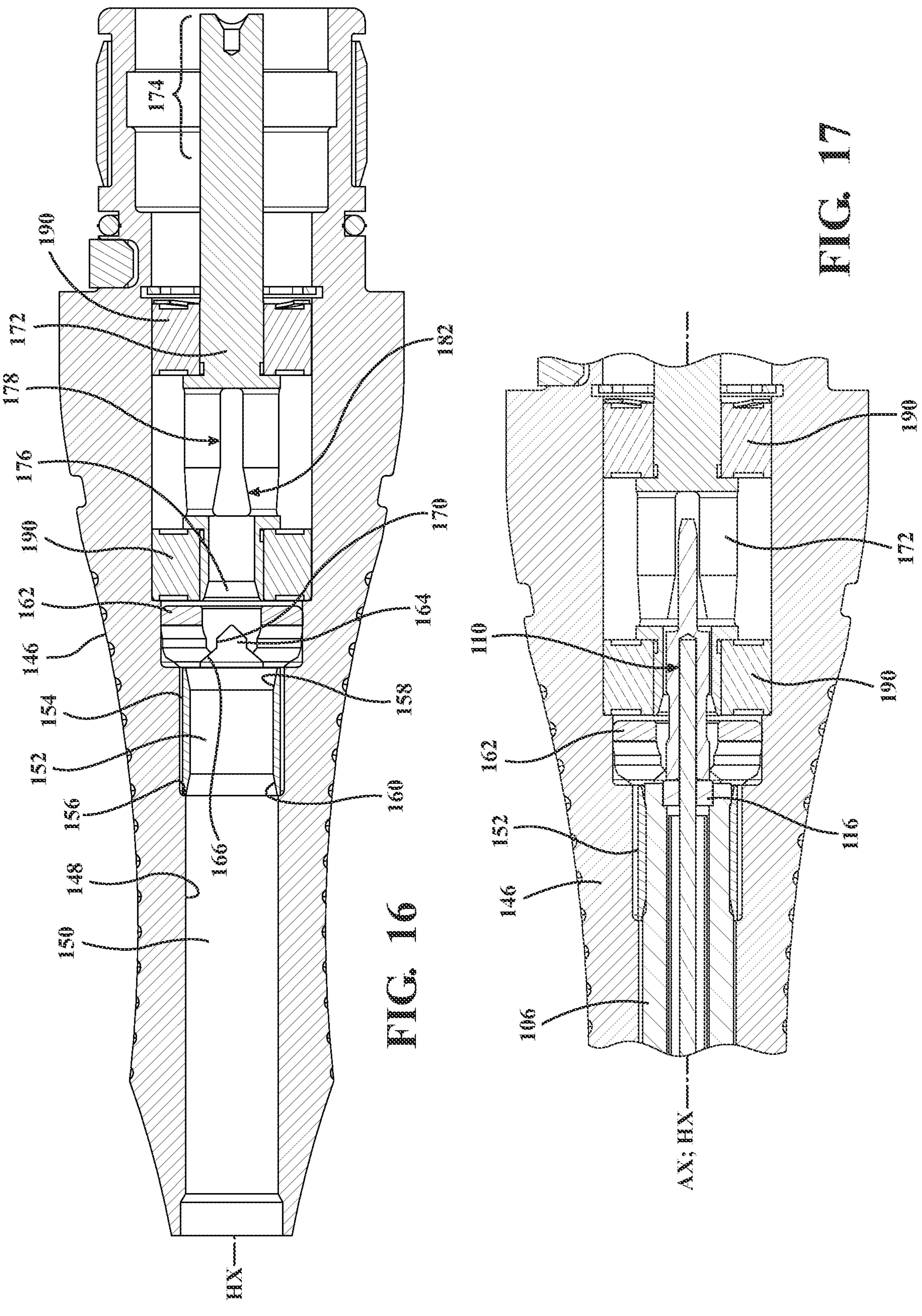
FIG. 16 is a sectional view of the surgical handpiece assembly of FIG. 14 taken along lines 16-16 of FIG. 14.
FIG. 17 is a partial sectional view of the surgical handpiece system of FIG. 9.

Referring to FIGS. 15 and 16, the surgical handpiece assembly 104 comprises a hub 146. The hub 146 has a bore 148 defining a cavity 150 for receiving at least part of the high-speed surgical bur assembly 102. Specifically, the cavity 150 is configured to receive at least the proximal portion 108 of the nose tube 106 and the proximal region 112 of the driveshaft 110 of the high-speed surgical bur assembly 102. A proximal portion of the hub 146 may be configured to be coupled to a motor housing (not shown) that includes a motor, similar of the motor 12 coupling to the hub 14 in the configuration illustrated in FIG. 1.

The surgical handpiece assembly 104 further comprises a biasing member 152 disposed within the cavity 150 of the hub 146. The biasing member 152 may be a C-clip. The bore 148 of the hub 146 may define a recess 154 in communication with the cavity 150. The recess 154 defined by bore 148 of the hub 146 is configured to receive the biasing member 152. The bore 148 of the hub 146 may have a distal shoulder 156 that defines a distal end of the recess 154 in the hub 146. The distal shoulder 156 retains the biasing member 152 from exiting the recess 154 of the hub 146 in a distal direction. When the high-speed surgical bur assembly 102 is received by the cavity 150 of the hub 146 of the surgical handpiece assembly 104, the biasing member 152 is received by the recess 124 of the nose tube 106. The biasing member 152 may be configured to engage one or both the proximal and distal shoulders 126, 128 of the recess 124 of the nose tube 106 to constrain a depth of the nose tube 106 of the high-speed surgical bur assembly 102 within the cavity 150 of the hub 146 relative to the hub 146. The biasing member 152 may have tapered surfaces 158, 160 on the proximal or distal ends to assist in engagement between the biasing member 152 and the nose tube 106.

Referring to FIGS. 18-20. The surgical handpiece assembly 104 may also comprise a radial alignment member 162 disposed within the cavity 150 of the hub 146 proximal to the biasing member 152. The radial alignment member 162 may be press-fit into the cavity 150 of the hub 146 such that no relative movement between the hub 146 and the radial alignment member 162 occurs. It is contemplated that the radial alignment member 162 and the hub 146 may be coupled to each other in another manner so long as no relative movement is permitted between the radial alignment member 162 and the hub 146.

The radial alignment member 162 defines a notch 164 for receiving the projection 130 of the nose tube 106 to constrain a radial orientation of the nose tube 106 relative to the hub 146. In the configuration illustrated in FIGS. 18-20, the radial alignment member 162 defines four notches 164 spaced circumferentially at equal angles relative to each other such that each notch 164 is spaced 90 (ninety) degrees from adjacent notches 164. It is contemplated that three or fewer notches 164 may be employed for receiving the projection 130 of the nose tube 106 to constrain a radial orientation of the nose tube 106 relative to the hub 146. It is also contemplated that five or more notches 164 may be used for receiving the projection 130 of the nose tube 106 to constrain a radial orientation of the nose tube 106 relative to the hub 146. Further, it is contemplated that the spacing between the notches 164 may be unequal and disposed at any position arranged circumferentially. It is appreciated that the number of notches 164 may determine the number of possible radial orientations of the nose tube 106 relative to the hub 146. Further, the spacing of the notches 164 may determine how far apart the radial orientations are. Permitting multiple orientations may be particularly advantageous when the nose tube 106 employs a bend. The bend may be oriented differently relative to the surgical handpiece assembly 104 based on which notch 164 of the radial alignment member 162 receives the projection 130 of the nose tube 106.

The radial alignment member 162 may have an alignment wall 166 extending distally from the notch 164 for engaging the projection 130 of the nose tube 106. The alignment wall 166 may radially position the nose tube 106 during engagement to permit the notch 164 to receive the projection 130 of the nose tube 106 if the projection 130 is not already radially aligned with the notch 164 of the radial alignment member 162. Two alignment walls 166 may be employed for each notch 164 of the radial alignment member 162; one on each side. Each of the two alignment walls 166 may taper inwardly toward the notch 164 such that contact between the alignment wall 166 of the radial alignment member 162 and the projection 130 of the nose tube 106 when the nose tube 106 is axially forced into the hub 146 results in relative rotation between the nose tube 106 and the hub 146 to orient the projection 130 into the notch 164. In configurations where the radial alignment member 162 comprises multiple alignment walls 166, consecutive alignment walls 166 between notches 164 may be tapered in opposite directions. The consecutive alignment walls 166 may also collectively form an edge 168 to mitigate a possibility of the projection 130 jamming into the radial alignment member 162 instead of radially positioning the projection 130 of the nose tube 106 into a notch 164 of the radial alignment member 162. Configurations where the projection 130 has a rounded surface 132 further assists in mitigating jamming with the radial alignment member 162.

As shown in FIG. 18, the radial alignment member 162 may also include one or more flat surfaces 170 to further define each notch 164. The flat surfaces 170 of the radial alignment member 162 may engage flat surfaces 134 of the projection 130 of the nose tube 106 when the projection 130 is received in the notch 164 to prevent relative rotation between the nose tube 106 and the hub 146. With relative rotation between the nose tube 106 and the hub 146 prevented, axial movement between the nose tube 106 and the hub 146 resulting from the relative rotation is also prevented.

In the configuration illustrated in FIG. 20, the radial alignment member 162 assists the distal shoulder 156 of the recess 154 of the hub 146 to retain the biasing member 152 in the recess 154 of the hub 146. As noted above, the distal shoulder 156 prevents the biasing member 152 from exiting the recess in a distal direction. With the radial alignment member 162 positioned immediately proximal the biasing member 152, the radial alignment member 162 forms a proximal shoulder of the recess 154 to prevent the biasing member 152 from exiting the recess 154 in a proximal direction. In other configurations, the bore 148 of the hub 146 may include a proximal shoulder (not shown) to define the proximal end of the recess 154 and the radial alignment member 162 may be positioned proximal to the proximal shoulder.

In some configurations, the biasing member 152 is configured to engage the distal shoulder 156 of the hub 146 and the proximal shoulder 126 of the nose tube 106 when the nose tube 106 is inserted in the cavity 150 of the hub 146 to force the projection 130 of the nose tube 106 toward the notch 164 of the radial alignment member 162. If the projection 130 is already partly received by the notch 164, engagement between the biasing member 152 and the shoulders 126, 156 may force the projection 130 deeper into the notch 164 until engagement ceases or until the projection 130 abuts a proximal surface of the notch 164 and is fully received by the notch 164.

As shown in FIG. 16, the surgical handpiece assembly 104 also comprises a rotatable drive chuck 172. The rotatable drive chuck 172 is configured to be rotated by a motor about a hub axis HX. A proximal portion 174 of the rotatable drive chuck 172 may engage a motor directly or the rotatable drive chuck 172 may engage a gear assembly or another assembly driven by a motor and configured to transfer torque from the motor to the rotatable drive chuck 172. The rotatable drive chuck 172 is disposed at least partially within the cavity 150 of the hub 146 proximal to the radial alignment member 162 and configured to rotate relative to the hub 146. The rotatable drive chuck 172 defines an opening 176 for receiving the proximal region 112 of the driveshaft 110.

Figures 23, 24, 25:
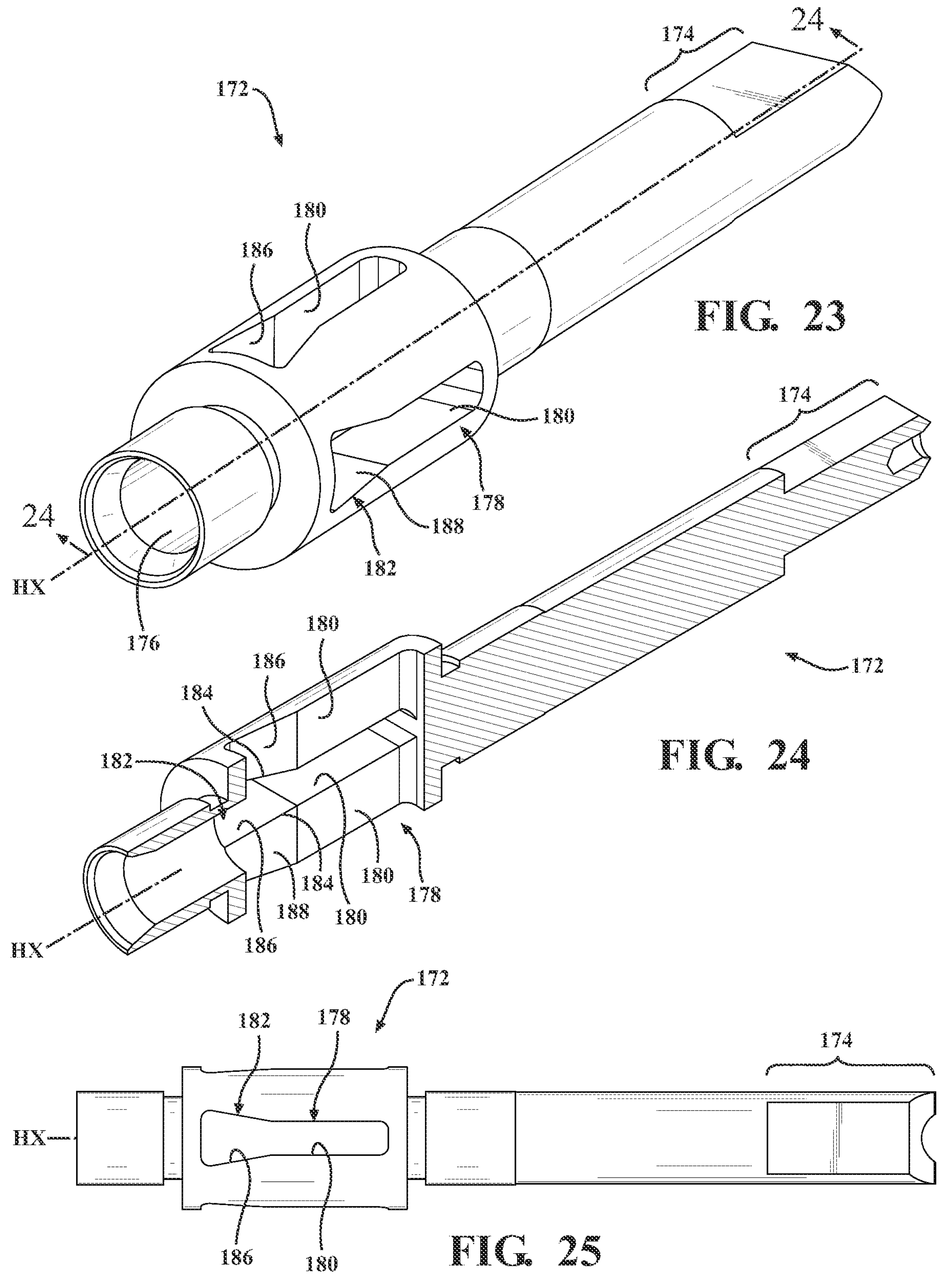
FIG. 23 is a perspective view of a rotatable drive chuck of the surgical handpiece assembly of FIG. 14.
FIG. 24 is a perspective section view of the rotatable drive chuck of FIG. 23 taken along lines 24-24 of FIG. 24.
FIG. 25 is a plan view of the rotatable drive chuck of FIG. 23.

As shown in FIGS. 23-25, the rotatable drive chuck 172 comprises a driving portion 178 proximal of the opening 176. The driving portion 178 has at least two driving surfaces 180 configured to engage the drive portion 136 of the proximal region 112 of driveshaft 110 to rotate the driveshaft 110. The driving surfaces 180 of the driving portion 178 of the rotatable drive chuck 172 engage the drive surfaces 138 of the drive portion 136 of the driveshaft 110 when the driveshaft 110 is in the driving orientation and the high-speed surgical bur assembly 102 is coupled to the surgical handpiece assembly 104 (see FIG. 17). The driveshaft 110 is in the driving orientation when the drive surfaces 138 of the driveshaft 110 are parallel to driving surfaces 180 of the driving portion 178 of the rotatable drive chuck 172. In the configuration illustrated in FIGS. 23-25, the driving portion 178 comprises eight driving surfaces 180 to accommodate various orientations of the drive portion 136 of the driveshaft 110. It is contemplated that there are multiple driving orientations when there are more than two driving surfaces 180. For instance, in the configuration illustrated in FIGS. 23-25, there are four different driving orientations. Said differently, the driveshaft 110 may be rotated by the rotatable drive chuck 172 in four different radial orientations relative to the rotatable drive chuck 172. It is also contemplated that the driving portion 178 may instead comprise between three and seven driving surfaces 180 to engage the drive portion 136 of the driveshaft 110. It is also contemplated that the driving portion 178 may instead comprise nine or more driving surfaces 180 to engage the drive portion 136 of the driveshaft 110.

The rotatable drive chuck 172 may also comprise an aligning portion 182 disposed between the driving portion 178 and the opening 176 of the rotatable drive chuck 172. The aligning portion 182 may have an alignment edge 184 extending distally from the driving portion 178 of the rotatable drive chuck 172 toward the opening of the rotatable drive chuck 172. The alignment edge 184 tapers away from the hub axis HX as the alignment edge 184 extends distally from the driving portion 178 of the rotatable drive chuck 172. The alignment edge 184 of the aligning portion 182 is configured to engage the alignment portion 140 of the driveshaft 110 to rotate the driveshaft 110 into the driving orientation.

The aligning portion 182 of the rotatable drive chuck 172 may have a first ramped surface 186 extending distally from the driving portion 178 of the rotatable drive chuck 172 toward the opening 176 of the rotatable drive chuck 172. The first ramped surface 186 tapers away from the hub axis HX as the first ramped surface 186 extends distally from the driving portion 178 of the rotatable drive chuck 172. The aligning portion 182 of the rotatable drive chuck 172 may have a second ramped surface 188 distinct from and adjacent to the first ramped surface 186. The second ramped surface 188 extends distally from the driving portion 178 of the rotatable drive chuck 172 toward the opening 176 of the rotatable drive chuck 172. The second ramped surface 188 tapers away from the hub axis HX as the second ramped surface 188 extends distally from the driving portion 178 of the rotatable drive chuck 172. The first and second ramped surfaces 186, 188 collectively define the alignment edge 184 of the rotatable drive chuck 172. In the configuration illustrated in FIGS. 23-25, the aligning portion 182 comprises four alignment edges 184. Each alignment edge 184 is formed by a first ramped surface 186 and a second ramped surface 188. In other configurations, the aligning portion 182 of the rotatable drive chuck 172 comprises three or fewer alignment edges 184. In still other configurations, the aligning portion 182 comprises five or more alignment edges 184. In some configurations, the first and second ramped surfaces 186, 188 are symmetrical about the alignment edge 184. In other configurations, the first and second ramped surfaces 186, 188 are not symmetrical about the alignment edge 184.

In one exemplary configuration, coupling between the high-speed surgical bur assembly 102 and the surgical handpiece assembly 104 is described below. A user may grasp the nose tube 106 of the high-speed surgical bur assembly 102 or another portion of the high-speed surgical bur assembly 102 and axially load (i.e., insert) the proximal portion 108 of the nose tube 106 and the proximal region 112 of the driveshaft 110 into the cavity 150 of the hub 146 of the surgical handpiece assembly 104. After the nose tube 106 and driveshaft 110 have entered the cavity 150 to a certain depth, the nose tube 106 is radially and axially constrained relative to the hub 146 of the surgical handpiece assembly 104 and the driveshaft 110 is radially and axially constrained relative to the rotatable drive chuck 172 of the surgical handpiece assembly 104. The constraints will be discussed in greater detail further below. As noted above, the driveshaft 110 is axially constrained to the nose tube 106 by the proximal and distal bushings 116, 118 of the high-speed surgical bur assembly 102. Further, the rotatable drive chuck 172 is axially constrained within the cavity 150 of the hub 146 by bushings 190 (see FIG. 15) coupled to the hub 146. As such, the driveshaft 110 is axially constrained relative to the rotatable drive chuck 172 when the nose tube 106 is axially constrained to the hub 146. As for radially constraining the nose tube 106 and the driveshaft 110, the driveshaft 110 is radially constrained relative to the rotatable drive chuck 172 prior to the nose tube 106 being radially constrained to the hub 146. In other configurations, the driveshaft 110 and nose tube 106 may be radially constrained simultaneously. In still other configurations the nose tube 106 may be radially constrained before the driveshaft 110. After both the driveshaft 110 and the nose tube 106 are radially constrained the nose tube 106 is axially constrained. Below, one exemplary configuration of constraining the nose tube 106 and the driveshaft 110 are described.

As the driveshaft 110 of the high-speed surgical bur assembly 102 enters the cavity 150 of the hub 146 of the surgical handpiece assembly 104, the driveshaft 110 enters through the opening 176 of the rotatable drive chuck 172. After entering through the opening 176 of the rotatable drive chuck 172, the outer surface of the alignment portion 140 of the driveshaft 110 abuts one of the alignment edges 184 of the aligning portion 182 of the rotatable drive chuck 172. As the driveshaft 110 continues to be axially loaded into the cavity 150 of the hub 146, the engagement between the alignment portion 140 of the driveshaft 110 and the alignment edge 184 of the rotatable drive chuck 172 orients the drive portion 136 of the driveshaft 110 to the driving orientation. In the driving orientation, the drive surfaces 138 of the driveshaft 110 may engage the driving surfaces 180 of the rotatable drive chuck 172 to radially constrain the driveshaft 110 to the rotatable drive chuck 172. When the drive surfaces 138 engage the driving surfaces 180, torque may be transferred from the rotatable drive chuck 172 to the driveshaft 110 and ultimately to the cutting tool 114.

Figure 26:
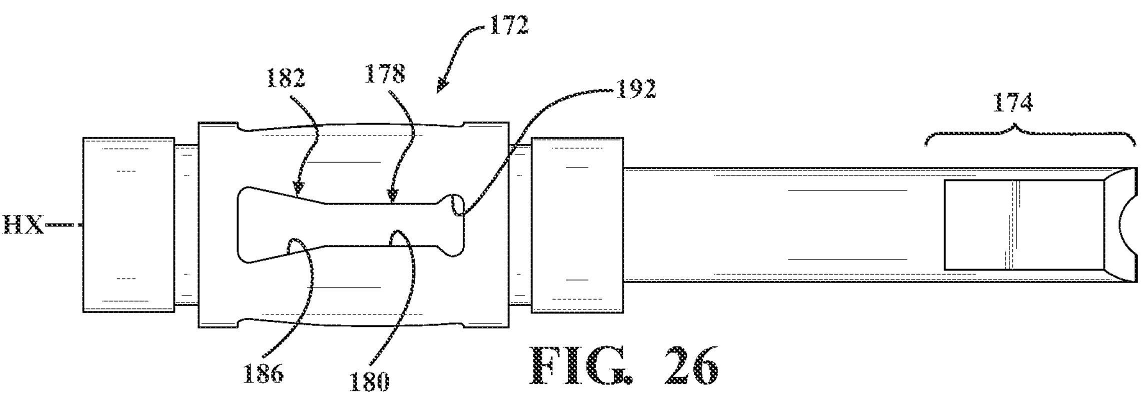
FIG. 26 is a plan view of another configuration of the rotatable drive chuck.

In one configuration illustrated in FIG. 26, the rotatable drive chuck 172 may define a cut-out 192 for providing additional clearance between the rotatable drive chuck 172 and the proximal end of the driveshaft 110 when the high-speed surgical bur assembly 102 is coupled to the surgical handpiece assembly 104. The additional clearance provided by the cut-out 192 may mitigate the chance that engagement between the proximal end of the driveshaft 110 and a surface of the rotatable drive chuck 172 occurs before the nose tube 106 is axially constrained to the hub 146. In other words, the additional clearance provided by the cut-out 192 ensures that continued insertion of the driveshaft 110 in the rotatable drive chuck 172 does not interfere with axial coupling of the nose tube 106 to the hub 146.

Engagement between the alignment portion 140 of the driveshaft 110 and the aligning portion 182 of the rotatable drive chuck 172 may permit rotation of the driveshaft 110 to the driving orientation to be accomplished exclusively by the user axially loading the high-speed surgical bur assembly 102 into the cavity 150 of the hub 146 of the surgical handpiece assembly 104. In other words, the driveshaft 110 may be oriented to the driving orientation without a user grasping the cutting tool 114 or another portion of the driveshaft 110 to manipulate the driveshaft 110 to the driving orientation. It is contemplated that in some instances, the driveshaft 110 will enter the cavity 150 of the hub 146 in the driving orientation. In such an instance, the alignment portion 140 of the driveshaft 110 may not contact the aligning portion 182 of the rotatable drive chuck 172 and the driveshaft 110 may not engage anything until the drive portion 136 of the driveshaft 110 engages the driving portion 178 of the rotatable drive chuck 172.

Figure 21:
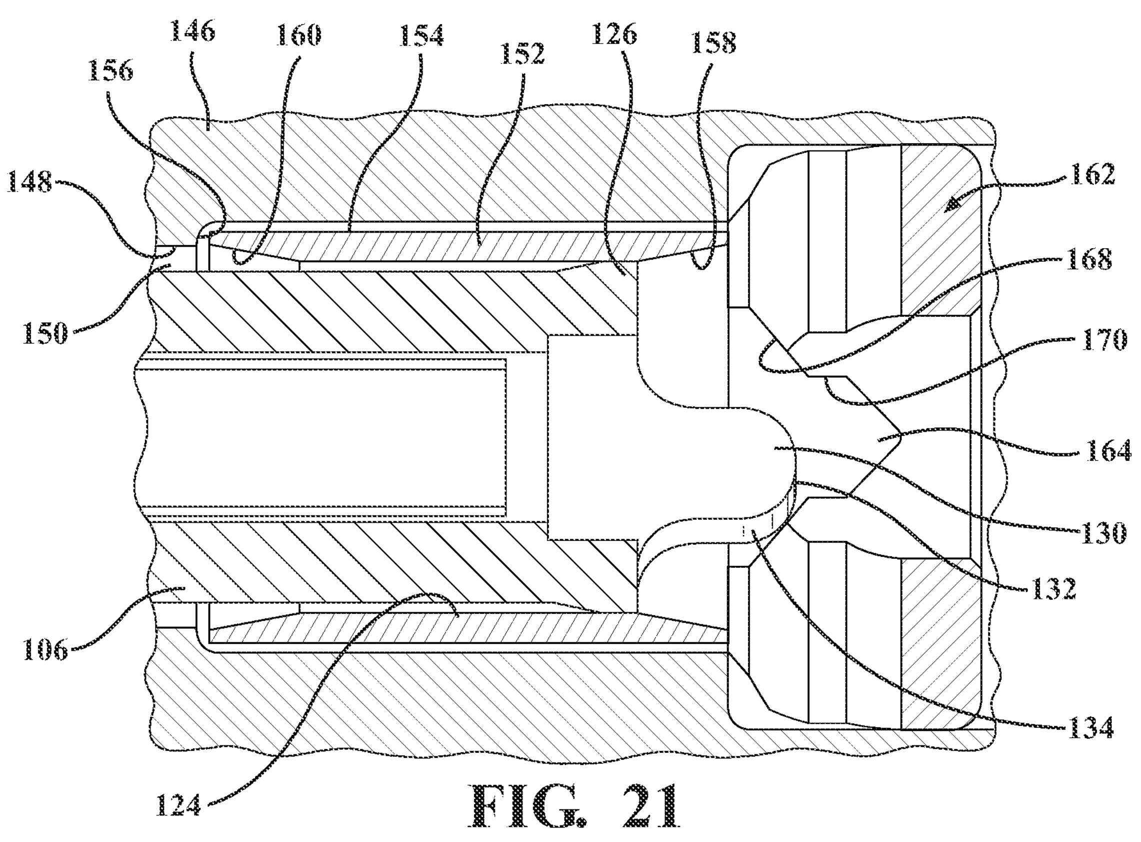
FIG. 21 is a detailed sectional view of the surgical handpiece assembly of FIG. 14 with the high-speed surgical bur assembly partially inserted in the cavity of the hub of the surgical handpiece assembly.
Figure 22:
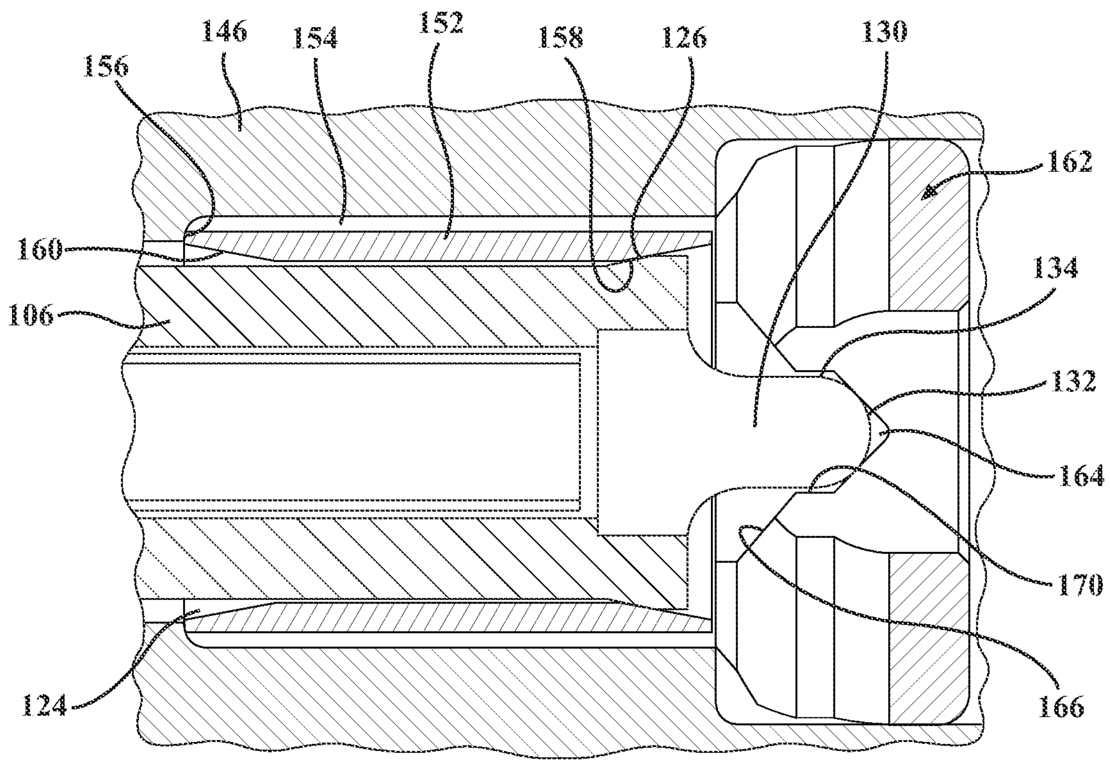
FIG. 22 is a detailed sectional view of the surgical handpiece assembly of FIG. 14 with the high-speed surgical bur assembly fully inserted in the cavity of the hub of the surgical handpiece assembly.

As shown in FIGS. 20-22, the nose tube 106 being axially and radially constrained, is illustrated. The driveshaft 110 in FIGS. 20-22 has been removed to better illustrate the engagement between the nose tube 106 and the surgical handpiece assembly 104. Referring to FIG. 20, the surgical handpiece assembly 104 is shown with the hub 146, the radial alignment member 162, and the biasing member 152. The biasing member 152 is shown in an unbiased, compressed state. As the nose tube 106 enters the cavity 150 of the hub 146 of the surgical handpiece assembly 104, the nose tube 106 engages the biasing member 152 by abutting the distal tapered surface 160 of the biasing member 152. When a sufficient axial force is applied to the nose tube 106 to overcome a spring force of the biasing member 152, the biasing member 152 expands to a biased state shown in FIG. 21 to accommodate the proximal portion 108 of the nose tube 106. In many instances, the projection 130 of the nose tube 106 may be misaligned and may engage the alignment wall 166 of the radial alignment member 162 such that continued axial force applied to the nose tube 106 may result in relative rotation between the nose tube 106 and the hub 146 until the projection 130 is aligned with notch 164. In other words, the nose tube 106 may be oriented so that the projection 130 of the nose tube 106 may be received by the notch 164 of the radial alignment member 162 without a user grasping the nose tube 106 to radially manipulate the nose tube 106.

In some configurations, as shown in FIG. 22, the biasing member 152 may be received in the recess 124 of the nose tube 106 and the proximal tapered surface 158 of the biasing member 152 may abut a proximal shoulder 126 of the recess on the nose tube 106 when the nose tube 106 is at a certain depth in the cavity 150 of the hub 146. When the proximal tapered surface 158 of the biasing member 152 abuts the proximal shoulder 126 of the recess 124 of the nose tube 106 and a distal end of the biasing member 152 abuts the distal shoulder 156 of the recess 154 of the hub 146, the spring force of the biasing member 152 may be sufficient to engage the nose tube 106 to force the projection 130 of the nose tube 106 deeper into the notch 164 of the radial alignment member 162. If the biasing member 152 has not returned to the unbiased, compressed state and the projection 130 of the nose tube 106 is fully received by the notch 164 of the radial alignment member 162 such that axial movement of the nose tube 106 in the proximal direction relative to the hub 146 is prevented, the biasing member 152 may continue to engage the nose tube 106 to axially constrain the nose tube 106 relative to the hub 146 and to keep a tight axial fit between the hub 146, the biasing member 152, the radial alignment member 162, and the nose tube 106. The tight axial fit may eliminate gaps that may have otherwise been present. Such gaps may have been formed from wear, tolerance stack-up, etc. In other configurations, the recess 124 of the nose tube 106 receives the biasing member 152 and the biasing member 152 constrains the depth of the nose tube 106 relative to the hub 146. In such a configuration, the biasing member 152 does not continue to engage the nose tube 106 to keep a tight axial fit between the hub 146, the biasing member 152, the radial alignment member 162, and the nose tube 106.

It is contemplated that in some instances, the nose tube 106 will enter the cavity 150 of the hub 146 in a radial orientation such that the projection 130 of the nose tube 106 may be received by the notch 164 of the radial alignment member 162 without rotating the nose tube 106. In such an instance, the projection 130 of the nose tube 106 may not contact the alignment wall 166 of the radial alignment member 162 and the projection 130 of the nose tube 106 may not engage anything until the projection 130 of the nose tube 106 is received by the notch 164 of the radial alignment member 162.

It will be further appreciated that the terms “include,” “includes,” and “including” have the same meaning as the terms “comprise,” “comprises,” and “comprising.” Moreover, it will be appreciated that terms such as “first,” “second,” “third,” and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The disclosure is intended to be defined in the independent claims, with specific features laid out in the dependent claims, wherein the subject-matter of a claim dependent from one independent claim can also be implemented in connection with another independent claim.

The present disclosure also comprises the following clauses, with specific features laid out in dependent clauses that may specifically be implemented as described in greater detail with reference to the configurations and drawings above.

Clauses

I. A high-speed surgical bur assembly for connection to a surgical handpiece comprising:

a nose tube defining a lumen, the lumen having a proximal portion having a longitudinal axis, and the nose tube having an outer surface defining a recess for receiving a biasing member to constrain a depth of the nose tube relative to the surgical handpiece, the nose tube including at least one projection distal the recess, the projection configured for radially aligning the high-speed surgical bur assembly with the surgical handpiece;

a driveshaft being at least partially disposed within the lumen and having an alignment portion at a proximal region of the driveshaft that is configured to align a drive portion of the driveshaft into an orientation to engage a rotatable drive chuck, the driveshaft having a retaining portion distal the alignment and drive portions, the retaining portion having a diameter being greater than a diameter of the lumen such that the driveshaft is retained within the lumen of the nose tube; and a cutting tool coupled to a distal region of the driveshaft opposite the alignment portion.

II. The high-speed surgical bur assembly of clause I, wherein the projection extends radially to a peak relative to the longitudinal axis of the proximal portion of the lumen, and wherein a distance between the outer surface of the nose tube defining the recess and the longitudinal axis is less than a distance between a surface of the peak and the longitudinal axis.

III. The high-speed surgical bur assembly of any of clauses I-II, wherein the at least one projection includes a slanted surface to allow the peak of the projection to radially align the high-speed surgical bur assembly with the surgical handpiece.

IV. The high-speed surgical bur assembly of any of clauses I-III, wherein the peak defines a radius distal the slanted surface.

V. The high-speed surgical bur assembly of any of clauses I-IV, wherein the alignment portion of the driveshaft defines a leading edge that engages the rotatable drive chuck to align the drive portion of the driveshaft to the orientation to engage the rotatable drive chuck.

VI. The high-speed surgical bur assembly of clause V, wherein the leading edge is defined between at least two curved surfaces to allow the drive portion to cam into the orientation to engage the rotatable drive chuck.

VII. The high-speed surgical bur assembly of clause VI, wherein the at least two curved surfaces are asymmetric across the longitudinal axis.

VIII. A high-speed surgical handpiece assembly comprising:

a hub having a proximal end and a distal end opposite the proximal end, the hub having an internal surface defining a bore extending from the distal end to the proximal end, the internal surface defining an alignment channel in communication with the bore extending from the distal end toward the proximal end;

a retention element disposed within the bore proximal to the alignment channel;

a rotatable drive chuck disposed within the bore proximal to the retention element, the rotatable drive chuck having a drive chamber;

a nose tube defining a lumen extending between proximal and distal ends, the nose tube having an outer surface defining a recess surrounding the nose tube to constrain a depth of the nose tube relative to the hub when the recess is engaged by the retention element, the nose tube including at least one projection, the projection configured to be received by the alignment channel to align the nose tube to the hub;

a driveshaft being at least partially disposed within the lumen of the nose tube and having an alignment portion configured to align a drive portion of the driveshaft into an orientation to engage the drive chamber of the rotatable drive chuck; and a cutting tool coupled to the driveshaft.

IX. The high-speed surgical handpiece assembly of clause VIII, wherein the alignment portion of the driveshaft defines a leading edge that engages a ramped surface of the rotatable drive chuck to align the drive portion of the driveshaft in the orientation to engage the drive chamber of the rotatable drive chuck.

X. The high-speed surgical handpiece assembly of any of clauses VIII-IX, wherein the retention feature comprises a biasing member.

XI. The high-speed surgical handpiece assembly of any of clauses VIII-X, wherein the nose tube comprises a monolithic structure.

XII. The high-speed surgical handpiece assembly of clause XI, wherein the recess and the projection are formed from a metallic material.

XIII The high-speed surgical handpiece assembly of clause XII, wherein the monolithic nose tube is formed of the metallic material of the projection and the recess.

What is claimed:

1. A high-speed surgical bur assembly configured to cut tissue and to be coupled to a surgical handpiece assembly, the high-speed surgical bur assembly comprising:

a nose tube defining a lumen extending between proximal and distal ends of the nose tube, the nose tube having a proximal portion extending along an axis, the proximal portion of the nose tube having an outer surface defining a recess for receiving a biasing member of the surgical handpiece assembly to constrain a depth of the nose tube relative to the surgical handpiece assembly, and the nose tube comprising a projection disposed proximal to the recess, the projection configured to constrain a radial orientation of the nose tube relative to the surgical handpiece assembly to prevent relative rotation between the nose tube and the surgical handpiece assembly;

a driveshaft at least partially disposed within the lumen of the nose tube and configured to rotate relative to the nose tube, the driveshaft having a drive portion at a proximal region of the driveshaft for engaging a rotatable drive chuck of the surgical handpiece assembly, and the driveshaft having a retention portion distal to the drive portion;

a proximal bushing disposed at least partially within the lumen of the nose tube, the proximal bushing surrounding a portion of the drive shaft and being sized smaller than the retention portion to prevent movement of the driveshaft in a distal direction relative to the nose tube;

a cutting tool coupled to a distal region of the driveshaft opposite the drive portion, the cutting tool configured to rotate with the driveshaft relative to the nose tube in response to rotation of the rotatable drive chuck of the surgical handpiece assembly; and a distal bushing coupled to a distal region of the nose tube and extending distally outside the nose tube, the distal bushing surrounding a portion of the driveshaft proximal the cutting tool and being sized smaller than the cutting tool to prevent movement of the driveshaft in a proximal direction relative to the nose tube;

wherein the proximal and distal bushings axially constrain the driveshaft to the nose tube such that movement of the driveshaft relative to the nose tube in proximal and distal directions is prevented; and wherein the driveshaft further comprises an alignment portion proximal the drive portion of the driveshaft, the alignment portion configured to align the drive portion of the driveshaft with the rotatable drive chuck of the surgical handpiece assembly and permit engagement between the drive portion of the driveshaft and the rotatable drive chuck, and wherein the alignment portion defines a notch extending distally from the proximal end such that the notch is formed at the proximal end of the driveshaft for mitigating contact between the alignment portion of the driveshaft and the rotatable drive chuck during engagement of the alignment portion with the rotatable drive chuck.

2. The high-speed surgical bur assembly of claim 1, wherein the projection of the proximal portion of the nose tube extends proximally and generally parallel to the axis.

3. The high-speed surgical bur assembly of claim 1, wherein a proximal end of the projection of the proximal portion of the nose tube comprises a rounded surface.

4. The high-speed surgical bur assembly of claim 1, wherein the projection of the proximal portion of the nose tube includes a flat surface that is parallel to the axis of the proximal portion of the nose tube, the flat surface configured to abut a surface of the surgical handpiece assembly to prevent relative rotation between the nose tube and the surgical handpiece assembly.

5. The high-speed surgical bur assembly of claim 1, wherein the alignment portion has an outer surface tapering toward the axis as the alignment portion extends from the drive portion to a proximal end of the driveshaft, the alignment portion configured to engage the rotatable drive chuck of the surgical handpiece assembly to align the drive portion to a driving orientation for the drive portion of the driveshaft to engage the rotatable drive chuck.

6. The high-speed surgical bur assembly of claim 1, wherein the alignment portion comprises a proximal edge for engaging the rotatable drive chuck of the surgical handpiece assembly to align the drive portion to a driving orientation for the drive portion of the driveshaft to engage the rotatable drive chuck.

7. The high-speed surgical bur assembly of claim 6, wherein the alignment portion comprises a proximal surface disposed proximally of the proximal edge to prevent the proximal edge from further engagement with the rotatable drive chuck of the surgical handpiece assembly after the drive portion is aligned in the driving orientation.

8. The high-speed surgical bur assembly of claim 7, wherein the proximal surface comprises a planar surface perpendicular to the axis.

9. The high-speed surgical bur assembly of claim 1, wherein the outer surface of the proximal portion of the nose tube has a proximal shoulder that defines a proximal end of the recess, and wherein the proximal shoulder is tapered, and wherein the proximal shoulder is configured to engage the biasing member of the surgical handpiece assembly to force the nose tube into the surgical handpiece assembly.

10. The high-speed surgical bur assembly of claim 1, wherein the proximal region of the driveshaft comprises the retention portion, and wherein the retention portion is disposed outside of the lumen of the nose tube.

11. The high-speed surgical bur assembly of claim 1, further comprising a middle bushing disposed within the lumen of the nose tube between the proximal and distal bushings, the middle bushing preventing contact between the driveshaft and the nose tube within the lumen of the nose tube.

12. The high-speed surgical bur assembly of claim 11, wherein the middle bushing is fixed to the nose tube.

13. The high-speed surgical bur assembly of claim 11, wherein the proximal and distal bushings retain the middle bushing within the lumen of the nose tube.

14. The high-speed surgical bur assembly of claim 11, wherein the middle bushing is retained in the lumen of the nose tube by a bend in the nose tube and a corresponding bend of the middle bushing.

* * * * *